United States Patent [19]
Makino et al.

[11] Patent Number: 5,354,731
[45] Date of Patent: Oct. 11, 1994

[54] PYRIDINESULFONAMIDE DERIVATIVES AS HERBICIDES

[75] Inventors: Kenzi Makino; Katsushi Morimoto; Shigeaki Akiyama; Hideaki Suzuki; Takeshi Nagaoka, all of Funabashi; Koichi Suzuki, Shiraoka; Tsutomu Nawamaki, Shiraoka; Shigeomi Watanabe, Shiraoka, all of Japan

[73] Assignee: Nissan Chemical Industries Ltd., Tokyo, Japan

[21] Appl. No.: 833,700

[22] Filed: Feb. 11, 1992

Related U.S. Application Data

[62] Division of Ser. No. 606,311, Oct. 31, 1990, Pat. No. 5,116,405.

[30] Foreign Application Priority Data

Nov. 6, 1989 [JP] Japan .................. 1-288313
Jun. 11, 1990 [JP] Japan .................. 2-152325
Sep. 11, 1990 [JP] Japan .................. 2-240264

[51] Int. Cl.$^5$ .............. C07D 401/12; C07D 405/14; C07D 409/14; A01N 43/40
[52] U.S. Cl. ...................... 504/253; 546/279
[58] Field of Search ............ 546/279; 71/94, 90; 504/253

[56] References Cited

FOREIGN PATENT DOCUMENTS 0052856 6/1982 European Pat. Off. .
0184385 6/1986 European Pat. Off. .
0269141 6/1988 European Pat. Off. .
0301784 2/1989 European Pat. Off. .
303383 2/1989 European Pat. Off. .

OTHER PUBLICATIONS

Chemical Abstracts, vol. 108, No. 3, Jan. 18, 1988, Columbus, Ohio, U.S.A. Kimura, Fumio, et al. "Process for the Preparation of (triazinyl- and (pyrimidinylaminocarbonyl) pyridine–sulfonamides as herbicides" p. 607, col. 1, abstract No. 21 930s&Jpn.

*Primary Examiner*—Marianne M. Cintins
*Assistant Examiner*—P. G. Spivack
*Attorney, Agent, or Firm*—Oblon, Spivak, McClelland, Maier & Neustadt

[57] ABSTRACT

A pyridinesulfonamide derivative of the formula (I) and a salt thereof:

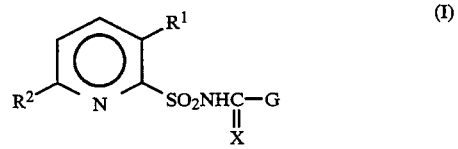

wherein $R^1$ is a halogen atom, a trifluoromethyl group, a $C_1$–$C_6$ alkoxycarbonyl group, a $C_1$–$C_6$ mono- or di-alkylaminocarbonyl group, a $C_1$–$C_6$ alkoxy group, a $C_1$–$C_6$ alkylsulfonyl group, a $C_1$–$C_6$ alkylthio group, a $C_1$–$C_6$ alkyl group substituted by a $C_1$–$C_6$ alkoxy group, a $C_1$–$C_6$ alkyl group substituted by a $C_1$–$C_6$ mono- or poly-halogenoalkoxy group, a $C_1$–$C_6$ mono- or poly-halogenoalkoxy group, a $C_1$–$C_6$ mono- or di-alkylaminosulfonyl group, a $C_1$–$C_6$ alkoxyaminosulfonyl group substituted by a $C_1$–$C_6$ alkyl group, a nitro group, a $C_1$–$C_6$ alkyl group substituted by a $C_1$–$C_6$ alkylthio group, a $C_1$–$C_6$ alkyl group substituted by a $C_1$–$C_6$ alkylsulfonyl group, or a $C_1$–$C_6$ alkyl group substituted by a $C_1$–$C_6$ alkoxycarbonyl group;

$R^2$ is a hydrogen atom or a halogen atom;
X is a oxygen atom or a sulfur atom; and
G is

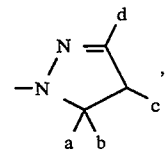

which are useful as herbicides.

13 Claims, No Drawings

PYRIDINESULFONAMIDE DERIVATIVES AS HERBICIDES

This is a division of application Ser. No. 07/606,311, filed on Oct. 31, 1990, now U.S. Pat. No. 5,116,405.

The present invention relates to novel pyridinesulfonamide derivatives and salts thereof, and herbicides containing such compounds as active ingredients.

It is indispensable to use herbicides to protect important crop plants such as rice, wheat, corn, soybean, cotton and sugar beet from weeds and thereby to increase the harvest. Especially in recent years, a selective herbicide is desired which is capable of selectively killing weeds without showing any phytotoxicity against crop plants when applied to the foliages of crop plants and weeds simultaneously in a field where such useful crop plants and weeds are coexistent. Further, with a view to avoiding environmental pollution and reducing the costs for transportation and application, researches and developments have been conducted for many years for compounds having high herbicidal effects at low doses. Some of the compounds having such properties are presently used as selective herbicides. However, there still exists a need for new compounds having such properties.

As the prior art showing a chemical structure similar to that of the compounds of the present invention, Japanese Unexamined Patent Publication No. 267576/1986 discloses pyridinesulfonylurea compounds, and Japanese Unexamined Patent Publication No. 122671/1988 discloses sufonamide compounds having a pyrazoline structure.

In Japanese Unexamined Patent Publication No. 122671/1988, heteroarylsulfonamide compounds are generally and broadly claimed on the basis of the disclosure of pyrazolesulfonamide derivatives and thiophenesulfonamide derivatives in addition to substituted benzene sulfonamide derivatives and substituted benzylsulfonamide derivatives, as sulfonamide compounds having a pyrazoline structure. However, in this publication, the compounds of the present invention are not specifically disclosed, and no specific description is given also as to the herbicidal activities of pyrazolesulfonamide derivatives although the usefulness of the heteroarylsulfonamide compounds are generally described.

Pyridinesulfonamide derivatives having a pyrazoline structure, like the compounds of the present invention, have not been known at all, and they are novel compounds.

The present inventors have conducted extensive researches over years to develop selective herbicides for important crop plants and have studied herbicidal properties of many compounds with an aim to find out compounds having higher herbicidal activities as well as selectivity. As a result, it has been found that pyridinesulfonamide derivatives of the following formula (I) and agriculturally suitable salts thereof (hereinafter referred to as the compounds of the present invention) exhibit remarkably strong herbicidal activities against many weeds in soil treatment or in foliage treatment and at the same time have a high level of safety for important crop plants such as wheat, corn, cotton, soybean, sugar beet and rice. The present invention has been accomplished on the basis of this discovery. On the other hand, since the compounds of the present invention show high herbicidal activities at a very low dose as compared with conventional herbicides, they are also useful as herbicides for orchards or for non-agricultural fields.

Namely, the present invention provides a pyridinesulfonamide derivative of the formula (I) and a salt thereof:

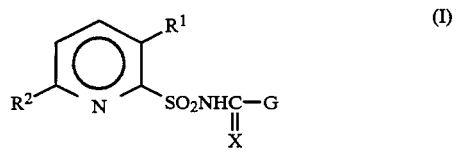

wherein $R^1$ is a halogen atom, a trifluoromethyl group, a $C_1$–$C_6$ alkoxycarbonyl group, a $C_1$–$C_6$ mono- or di-alkylaminocarbonyl group, a $C_1$–$C_6$ alkoxy group, a $C_1$–$C_6$ alkylsulfonyl group, a $C_1$–$C_6$ alkylthio group, a $C_1$–$C_6$ alkyl group substituted by a $C_1$–$C_6$ alkoxy group, a $C_1$–$C_6$ alkyl group substituted by a $C_1$–$C_6$ mono- or poly-halogenoalkoxy group, a $C_1$–$C_6$ mono- or poly-halogenoalkoxy group, a $C_1$–$C_6$ mono- or di-alkylaminosulfonyl group, a $C_1$–$C_6$ alkoxyaminosulfonyl group substituted by a $C_1$–$C_6$ alkyl group, a nitro group, a $C_1$–$C_6$ alkyl group substituted by a $C_1$–$C_6$ alkylthio group, a $C_1$–$C_6$ alkyl group substituted by a $C_1$–$C_6$ alkylsulfonyl group, or a $C_1$–$C_6$ alkyl group substituted by a $C_1$–$C_6$ alkoxycarbonyl group;

$R^2$ is a hydrogen atom or a halogen atom;

X is a oxygen atom or a sulfur atom; and

G is

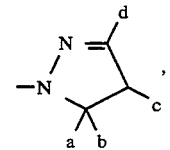

wherein each of a, b, c and d independently represents a hydrogen atom, a $C_1$–$C_6$ alkyl group, a $C_2$–$C_6$ alkenyl group, a $C_2$–$C_6$ alkynyl group, a $C_1$–$C_6$ alkyl group mono- or poly-substituted by a halogen atom, a $C_1$–$C_6$ alkoxy group, a $C_1$–$C_6$ alkyl group substituted by a $C_1$–$C_6$ alkoxy group, a $C_1$–$C_6$ alkoxycarbonyl group, a $C_1$–$C_6$ alkyl group substituted by a $C_1$–$C_6$ alkylthio group, a $C_1$–$C_6$ alkyl group substituted by a $C_1$–$C_6$ alkylsulfonyl group, a $C_1$–$C_6$ alkylthio group, a $C_1$–$C_6$ alkylcarbonyl group, a $C_3$–$C_7$ cycloalkyl group, a $C_3$–$C_7$ cycloalkenyl group, a cyano group, a phenyl or benzyl group (provided that this phenyl or benzyl group may be mono- or poly-substituted by a halogen atom, a trifluoromethyl group, a $C_1$–$C_6$ alkyl group, a $C_1$–$C_6$ alkoxy group, a $C_1$–$C_6$ alkoxycarbonyl group or a nitro group), a 5- or 6-membered heterocyclic group (provided that such a heterocyclic group contains from 1 to 3 hetero atoms selected from the group consisting of nitrogen atoms, oxygen atoms and sulfur atoms in the ring, or contains a sulfonyl group, and such a heterocyclic group may be mono- or poly-substituted by a $C_1$–$C_6$ alkyl group, a $C_1$–$C_6$ alkoxy group, a halogen atom, a trifluoromethyl group, a nitro group or a $C_1$–$C_6$ alkoxycarbonyl group), a naphthyl group, a benzene-condensed heterocyclic group (provided that such a benzene-condensed heterocyclic group contains 1 or 2 hetero atoms selected from the group consisting of nitrogen atoms, oxygen atoms and sulfur atoms in the ring, and such a benzene-condensed heterocyclic group may be mono- or poly-substituted by a $C_1$–$C_6$ alkyl group, a $C_1-C_6$ alkoxy group, a halogen atom, a trifluoromethyl group, a nitro group or a $C_1-C_6$ alkoxycarbonyl group).

The present invention also provides a selective herbicide containing one or more compounds of the present invention as active ingredients.

Now, the present invention will be described in detail with reference to the preferred embodiments.

The compounds of the formula (I) of the present invention can easily be prepared by any one of the following reaction schemes 1 to 3.

Reaction scheme 1

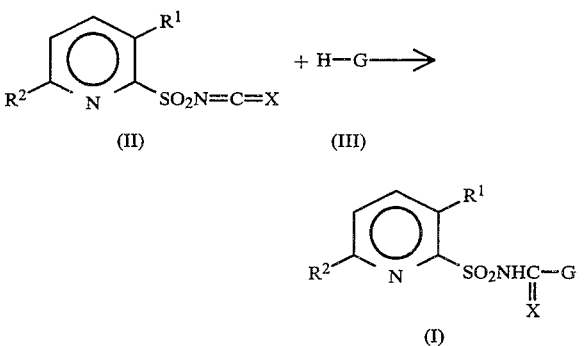

In the above formulas, $R^1$, $R^2$, G and X are as defined above.

Namely, a pyridinesulfonyliso(thio)cyanate derivative (II) is dissolved in a sufficiently dried inert solvent such as benzene, toluene, dichloromethane, dichloroethane, tetrahydrofuran, dioxane, acetonitrile, acetone or methyl ethyl ketone, then a pyrazoline derivative of the formula (III) is added thereto, and the mixture is stirred, whereby the reaction usually proceeds swiftly and the compound (I) of the present invention is obtained. When the reaction hardly proceeds, a very small amount of a suitable base such as triethylamine, triethylenediamine, pyridine, 1,8-diazabicyclo[5,4,0]-7-undecene (DBU), a sodium alkoxide, sodium hydride or potassium carbonate may be added, whereby the reaction readily proceeds.

Reaction scheme 2

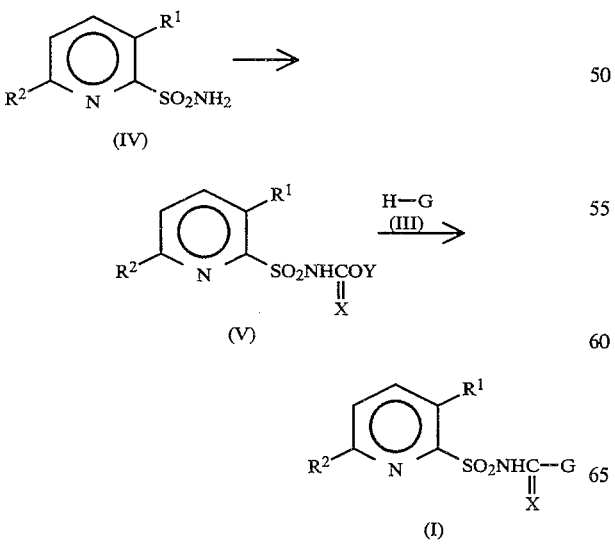

In the above formulas, $R^1$, $R^2$, G and X are as defined above, and Y is a $C_1-C_6$ alkyl group or a phenyl group.

Namely, a pyridinesulfonamide derivative (IV) is reacted with chloro(thio)formic acid ester or (thio)carbonic acid diester in a solvent such as acetone, methyl ethyl ketone, acetonitrile, tetrahydrofuran, dioxane, dichloromethane, dichloroethane, N,N-dimethylformamide, benzene or toluene in the presence of a base such as pyridine, triethylamine, 1,8-diazabicyclo[5,4,0]-7-undecene (DBU), potassium carbonate, a sodium alkoxide, sodium hydride, sodium hydroxide or potassium hydroxide to obtain a compound (V). Then, it is heated together with a compound (III) in a solvent such as tetrahydrofuran, dioxane, benzene, toluene, acetone, methyl ethyl ketone, dichloromethane, dichloroethane or N,N-dimethylformamide in the presence of a base such as pyridine, triethylamine, DBU, potassium carbonate, a sodium alkoxide, sodium hydride, sodium hydroxide or potassium hydroxide to obtain the compound (I) of the present invention.

Reaction scheme 3

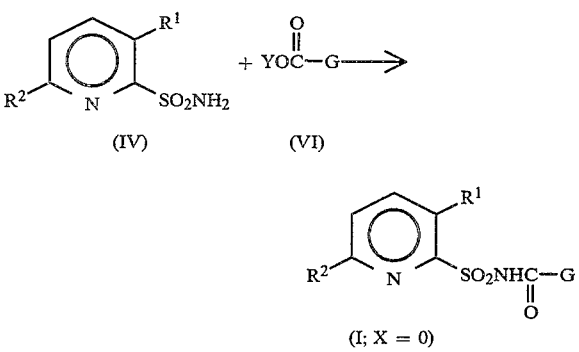

In the above formulas, $R^1$, $R^2$, G and Y are as defined above.

Namely, a pyridinesulfonamide derivative (IV) is reacted with a carbamate derivative (VI) in a solvent such as acetone, methyl ethyl ketone, acetonitrile, tetrahydrofuran, dioxane, dichloromethane, dichloroethane, N,N-dimethylformamide, benzene or toluene in the presence of an inorganic base such as potassium carbonate, sodium hydroxide or potassium hydroxide, or an organic base such as triethylamine, pyridine or DBU, to obtain the compound of the present invention (I; X=O).

The pyridinesulfonyliso(thio)cyanate derivative (II) to be used as a starting material in reaction scheme 1 can be synthesized from a pyridinesulfonamide derivative (IV) in accordance with the methods disclosed in e.g. Japanese Unexamined Patent Publications No. 148879/1983, No. 31775/1984 and No. 13266/1980.

The pyridinesulfonamide derivative (IV) to be used as a starting material in reaction schemes 2 and 3 can be synthesized in accordance with the methods disclosed in e.g. Japanese Unexamined Patent Publications No. 23180/1987 and No. 267576/1986.

The pyrazoline (III) to be used as a starting material for the above reactions, can readily be synthesized in accordance with e.g. Japanese Unexamined Patent Publication No. 122671/1988. Representative examples are shown as reaction schemes 4 and 5.

Reaction scheme 4

-continued

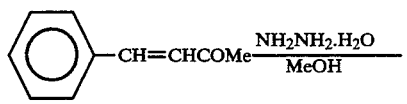

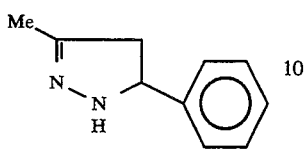

Reaction scheme 5

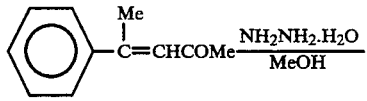

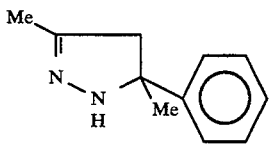

Now, the syntheses of the compounds of the present invention will be described in detail with reference to reference example and preparation example. However, it should be understood that the present invention is by no means restricted by such specific examples.

REFERENCE EXAMPLE

Preparation of methyl N-(3-trifluoromethylpyridine-2-sulfonyl)carbamate

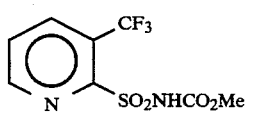

Methyl chloroformate (3.31 g, 35 mmol) was added under cooling with ice to a dry acetonitrile (150 ml) solution containing 3-trifluoromethylpyridine-2-sulfonamide (7.91 g, 35 mmol) and triethylamine (16 ml), and the mixture was continuously stirred at room temperature for 3 hours. Then, the solvent was distilled off under reduced pressure, and the residue was dissolved in 300 ml of water. A small amount of insoluble substances were removed by filtration, and the filtrate was adjusted to pH of 1 to 2 with concentrated hydrochloric acid under cooling with ice. Precipitated crystals were collected by filtration and thoroughly washed with water, then washed with a solvent mixture of ethyl ether/n-hexane and dried to obtain 4.4 g of desired methyl N-(3-trifluoromethylpyridine-2-sulfonyl)carbamate. Melting point: 128°–129° C.

PREPARATION EXAMPLE 1

Preparation of 1-(3-trifluoromethylpyridine-2-sulfonylcarbamoyl)-3-methyl-5-phenyl-2-pyrazoline

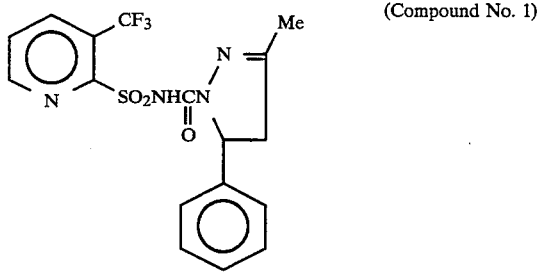

(Compound No. 1)

A dry dioxane (10 ml) solution containing methyl N-(3-trifluoromethylpyridine-2-sulfonyl)carbamate (0.43 g, 1.5 mmol), 3-methyl-5-phenyl-2-pyrazoline (0.48 g, 3.0 mmol) and pyridine (0.45 g) was refluxed under heating and stirring for one hour. After cooling the mixture, the solvent was distilled off under reduced pressure, and the residue was stirred together with ethyl ether. Precipitated crystals were collected by filtration and then thoroughly washed with ethyl ether, and the crystals were suspended in 20 ml of water. Then, the pH was adjusted to a level of from 1 to 2 with concentrated hydrochloric acid, and the suspension was stirred at room temperature for 5 minutes. Crystals were collected by filtration, thoroughly washed with water and then with ethyl ether and dried to obtain 0.51 g of desired 1-(3-trifluoromethylpyridine-2-sulfonylcarbamoyl)-3-methyl-5-phenyl-2-pyrazoline. Melting point: 185°–187° C.

PREPARATION EXAMPLE 2

Preparation of 1-(3-trifluoromethylpyridine-2-sulfonylcarbamoyl)-3,5-dimethyl-5-phenyl-2-pyrazoline

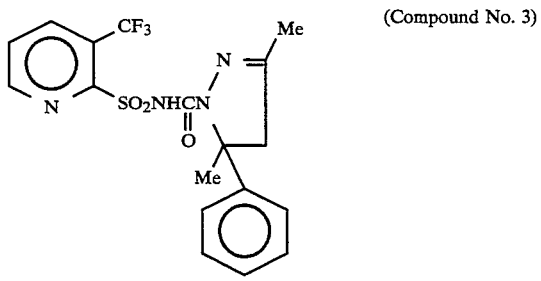

(Compound No. 3)

A dry dioxane (10 ml) solution containing methyl N-(3-trifluoromethylpyridine-2-sulfonyl)carbamate (0.43 g, 1.5 mmol), 3,5-dimethyl-5-phenyl-2-pyrazoline (0.52 g, 3.0 mmol) and pyridine (0.45 g) was refluxed under heating and stirring for one-hour. After cooling the mixture, the solvent was distilled off under reduced pressure, and the residue was stirred together with ethyl ether. Precipitated crystals were collected by filtration and then thoroughly washed with ethyl ether, and the crystals were suspended in 20 ml of water. Then, the pH was adjusted to a level of from 1 to 2 with concentrated hydrochloric acid, and the suspension was stirred at room temperature for 5 minutes. Crystals were collected by filtration, thoroughly washed with water and then with ethyl ether and dried to obtain 0.55 g of desired 1-(3-trifluoromethylpyridine-2-sulfonylcarbamoyl)-3,5-dimethyl-5-phenyl-2-pyrazoline. Melting point: 152°–153° C.

The structures and the physical values or properties of the compounds prepared in the same manner as the above preparation example are shown below.

Compound No. 1

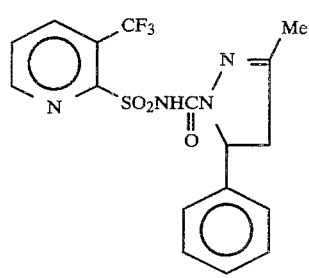

m.p. 185–187° C.

Compound No. 2 m.p. 183~184° C.

Compound No. 3 m.p. 152~153° C.

Compound No. 4 m.p. 160~161° C.

Compound No. 5 m.p. 177~178° C.

Compound No. 6

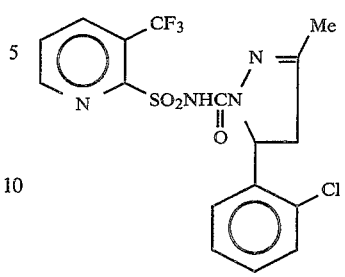

m.p. 144~145° C.

Compound No. 7

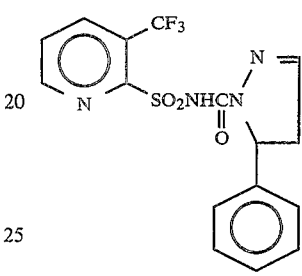

m.p. 138~140° C.

Compound No. 8

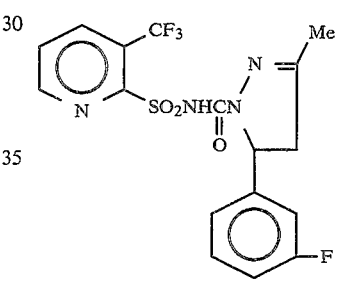

m.p. 185~186° C.

Compound No. 9

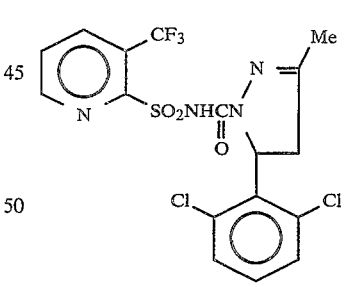

m.p. 195~196° C.

Compound No. 10

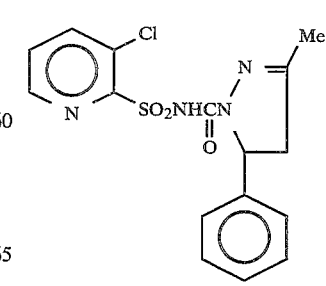

m.p. 157~158° C.

-continued
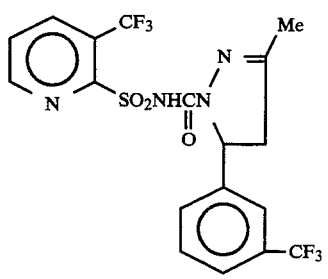
Compound No. 11
m.p. 150~151° C.
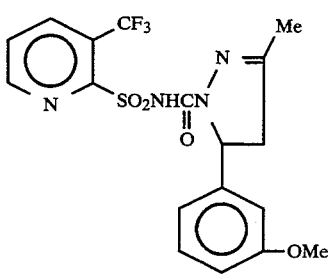
Compound No. 12
m.p. 129~130° C.
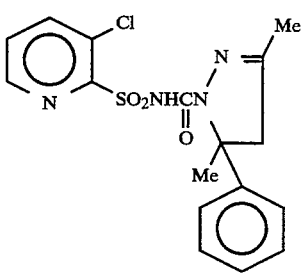
Compound No. 13
m.p. 178~179° C.
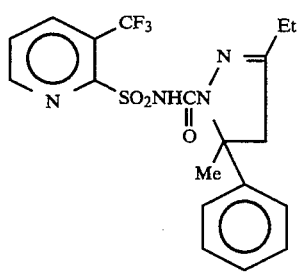
Compound No. 14
Oil
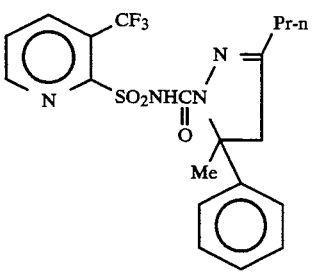
Compound No. 15
m.p. 149~150° C.
-continued
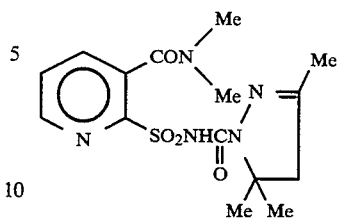
Compound No. 16
m.p. 207~208° C.
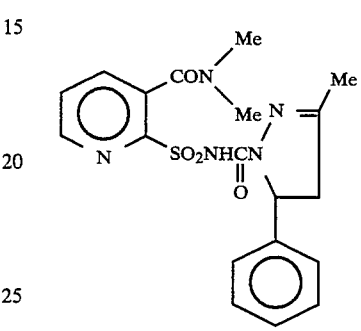
Compound No. 17
Glassy
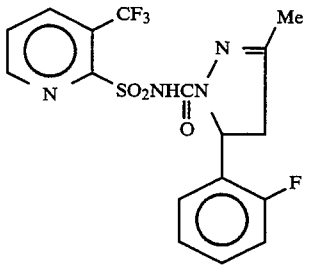
Compound No. 18
m.p. 168~170° C.
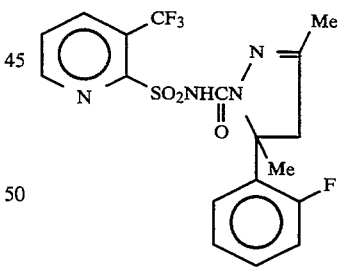
Compound No. 19
m.p. 168~169° C.
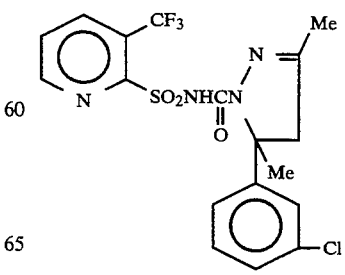
Compound No. 20
m.p. 116~117° C.

-continued
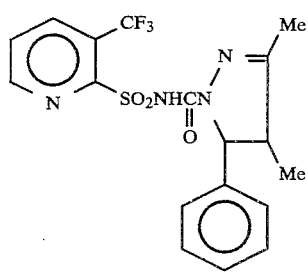
Compound No. 21
m.p. 178.5~179.5° C.
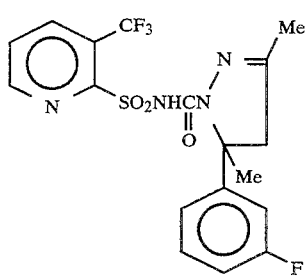
Compound No. 22
m.p. 136~137° C.
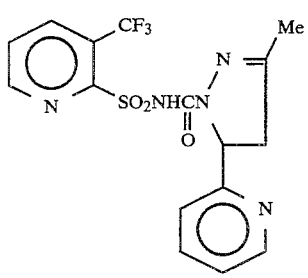
Compound No. 23
m.p. 177~178° C.
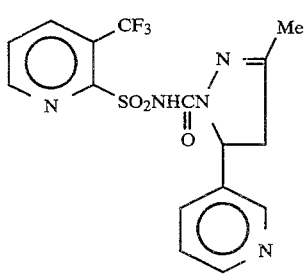
Compound No. 24
m.p. 186~187° C.
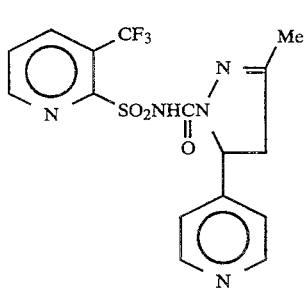
Compound No. 25
m.p. 188~189° C.
-continued
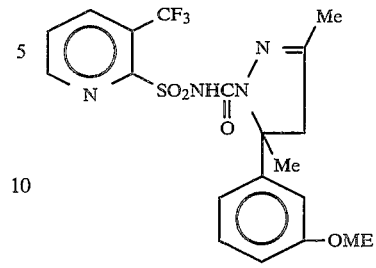
Compound No. 26
m.p. 106~107° C.
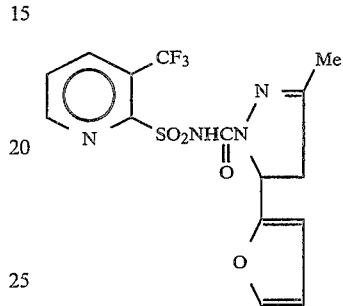
Compound No. 27
m.p. 136~137° C.
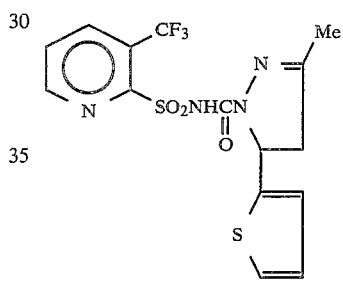
Compound No. 28
m.p. 124~125° C.
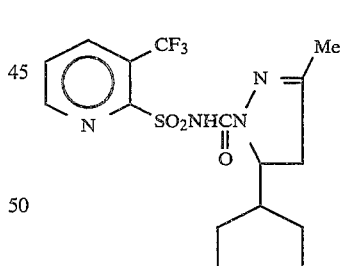
Compound No. 29
m.p. 160~161° C.
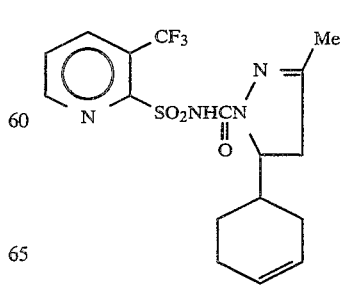
Compound No. 30
m.p. 113~114° C.

-continued

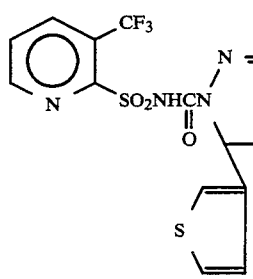

Compound No. 31 m.p. 177~178° C.

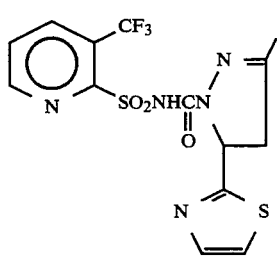

Compound No. 32 m.p. 187~188° C.

Now, Table 1 presents examples of specific compounds of the present invention including the compounds prepared in the preceding examples. However, it should be understood that the compounds of the present invention are not limited to such specific examples.

In Table 1, Gn in the structural formula has the same meaning as G and includes all of G1 to G479 as defined hereinafter, and the symbols used in the table have the following meanings:

Me: methyl group, Et: ethyl group, Pr-n: n-propyl group, Pr-i: isopropyl group, Bu-n: n-butyl group, Pen-n: n-pentyl group and Ph: phenyl group.

TABLE 1

| $R^1$ | $R^2$ | X |
|---|---|---|
| Cl | H | O |
| Cl | H | S |
| Cl | F | O |
| Cl | F | S |
| Cl | Cl | O |
| Cl | Cl | S |
| Br | H | O |
| Br | H | S |
| Br | F | O |
| Br | F | S |
| Br | Cl | O |
| Br | Cl | S |
| $CF_3$ | H | O |
| $CF_3$ | H | S |
| $CF_3$ | F | O |
| $CF_3$ | F | S |
| $CF_3$ | Cl | O |
| $CF_3$ | Cl | S |
| $CO_2Me$ | H | O |
| $CO_2Me$ | H | S |
| $CO_2Me$ | F | O |
| $CO_2Me$ | F | S |
| $CO_2Me$ | Cl | O |
| $CO_2Me$ | Cl | S |
| $CO_2Et$ | H | O |
| $CO_2Et$ | H | S |
| $CO_2Et$ | F | O |
| $CO_2Et$ | F | S |
| $CO_2Et$ | Cl | O |
| $CO_2Et$ | Cl | S |
| $CO_2Pr$-n | H | O |
| $CO_2Pr$-n | H | S |
| $CO_2Pr$-n | F | O |
| $CO_2Pr$-n | F | S |
| $CO_2Pr$-n | Cl | O |
| $CO_2Pr$-n | Cl | S |
| $CONMe_2$ | H | O |
| $CONMe_2$ | H | S |
| $CONMe_2$ | F | O |
| $CONMe_2$ | F | S |
| $CONMe_2$ | Cl | O |
| $CONMe_2$ | Cl | S |
| OMe | H | O |
| OMe | H | S |
| OMe | F | O |
| OMe | F | S |
| OMe | Cl | O |
| OMe | Cl | S |
| OEt | H | O |
| OEt | H | S |
| OEt | F | O |
| OEt | F | S |
| OEt | Cl | O |
| OEt | Cl | S |
| $SO_2Me$ | H | O |
| $SO_2Me$ | H | S |
| $SO_2Me$ | F | O |
| $SO_2Me$ | F | S |
| $SO_2Me$ | Cl | O |
| $SO_2Me$ | Cl | S |
| $SO_2Et$ | H | O |
| $SO_2Et$ | H | S |
| $SO_2Et$ | F | O |
| $SO_2Et$ | F | S |
| $SO_2Et$ | Cl | O |
| $SO_2Et$ | Cl | S |
| SMe | H | O |
| SMe | H | S |
| SMe | F | O |
| SMe | F | S |
| SMe | Cl | O |
| SMe | Cl | S |
| $CH_2OMe$ | H | O |
| $CH_2OMe$ | H | S |
| $CH_2OMe$ | F | O |
| $CH_2OMe$ | F | S |
| $CH_2OMe$ | Cl | O |
| $CH_2OMe$ | Cl | S |
| $CH_2OEt$ | H | O |
| $CH_2OEt$ | H | S |
| $CH_2OEt$ | F | O |
| $CH_2OEt$ | F | S |
| $CH_2OEt$ | Cl | O |
| $CH_2OEt$ | Cl | S |
| $CH_2OCHF_2$ | H | O |
| $CH_2OCHF_2$ | H | S |
| $CH_2OCHF_2$ | F | O |
| $CH_2OCHF_2$ | F | S |
| $CH_2OCHF_2$ | Cl | O |
| $CH_2OCHF_2$ | Cl | S |
| $CH_2OCH_2CF_3$ | H | O |
| $CH_2OCH_2CF_3$ | H | S |
| $CH_2OCH_2CF_3$ | F | O |
| $CH_2OCH_2CF_3$ | F | S |
| $CH_2OCH_2CF_3$ | Cl | O |
| $CH_2OCH_2CF_3$ | Cl | S |
| $OCH_2CH_2Cl$ | H | O |
| $OCH_2CH_2Cl$ | H | S |

TABLE 1-continued

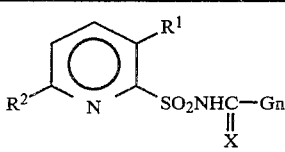

| R¹ | R² | X |
|---|---|---|
| OCH₂CH₂Cl | F | O |
| OCH₂CH₂Cl | F | S |
| OCH₂CH₂Cl | Cl | O |
| OCH₂CH₂Cl | Cl | S |
| SO₂NMe₂ | H | O |
| SO₂NMe₂ | H | S |
| SO₂NMe₂ | F | O |
| SO₂NMe₂ | F | S |
| SO₂NMe₂ | Cl | O |
| SO₂NMe₂ | Cl | S |
| SO₂N(OMe)Me | H | O |
| SO₂N(OMe)Me | H | S |
| SO₂N(OMe)Me | F | O |
| SO₂N(OMe)Me | F | S |
| SO₂N(OMe)Me | Cl | O |
| SO₂N(OMe)Me | Cl | S |
| NO₂ | H | O |
| NO₂ | H | S |
| NO₂ | F | O |
| NO₂ | F | S |
| NO₂ | Cl | O |
| NO₂ | Cl | S |
| CH₂SMe | H | O |
| CH₂SMe | H | S |
| CH₂SMe | F | O |
| CH₂SMe | F | S |
| CH₂SMe | Cl | O |
| CH₂SMe | Cl | S |
| CH₂SEt | H | O |
| CH₂SEt | H | S |
| CH₂SEt | F | O |
| CH₂SEt | F | S |
| CH₂SEt | Cl | O |
| CH₂SEt | Cl | S |
| CH₂SO₂Me | H | O |
| CH₂SO₂Me | H | S |
| CH₂SO₂Me | F | O |
| CH₂SO₂Me | F | S |
| CH₂SO₂Me | Cl | O |
| CH₂SO₂Me | Cl | S |
| CH₂SO₂Et | H | O |
| CH₂SO₂Et | H | S |
| CH₂SO₂Et | F | O |
| CH₂SO₂Et | F | S |
| CH₂SO₂Et | Cl | O |
| CH₂SO₂Et | Cl | S |
| CH₂CO₂Me | H | O |
| CH₂CO₂Me | H | S |
| CH₂CO₂Me | F | O |
| CH₂CO₂Me | F | S |
| CH₂CO₂Me | Cl | O |
| CH₂CO₂Me | Cl | S |
| CH₂CO₂Et | H | O |
| CH₂CO₂Et | H | S |
| CH₂CO₂Et | F | O |
| CH₂CO₂Et | F | S |
| CH₂CO₂Et | Cl | O |
| CH₂CO₂Et | Cl | S |

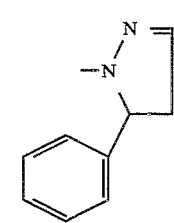

G1

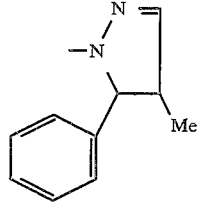

G2

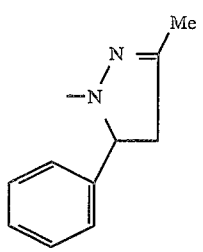

G3

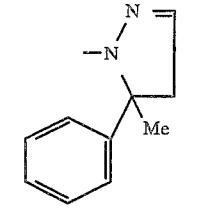

G4

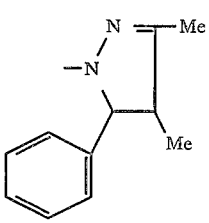

G5

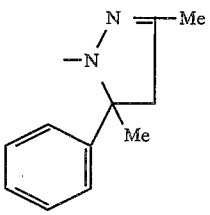

G6

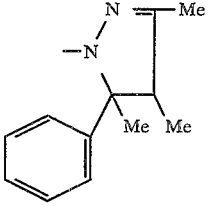

G7

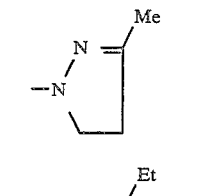

G8

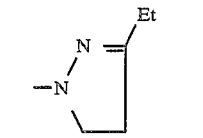

G9

-continued
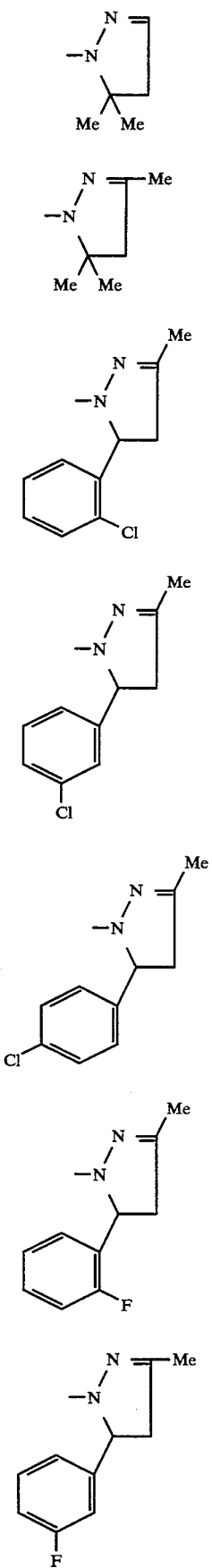
G10
G11
G12
G13
G14
G15
G16
-continued
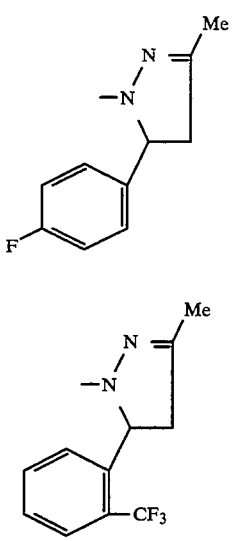
G17
G18
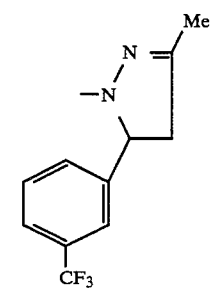
G19
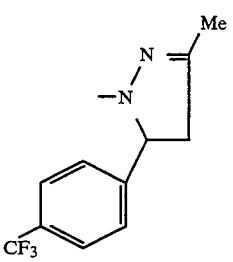
G20
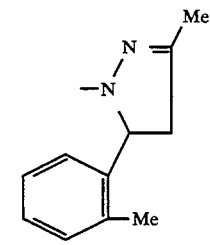
G21
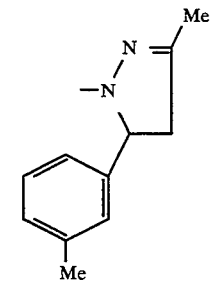
G22

-continued
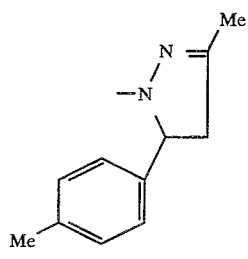 G23
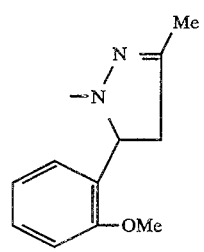 G24
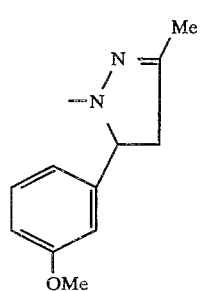 G25
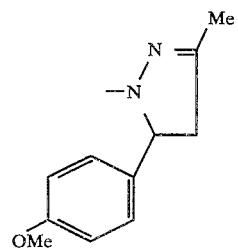 G26
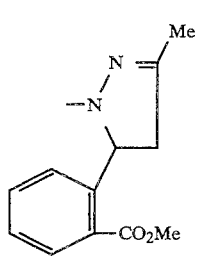 G27
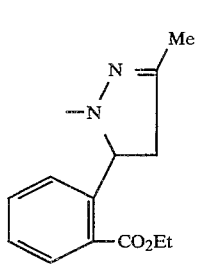 G28
-continued
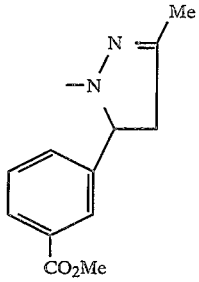 G29
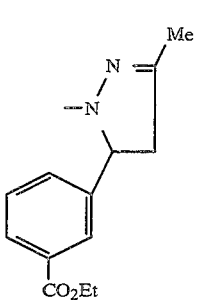 G30
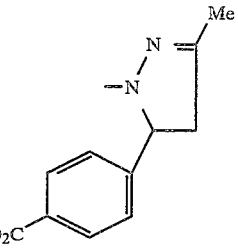 G31
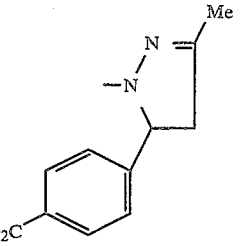 G32
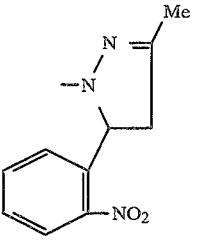 G33
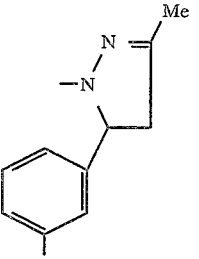 G34

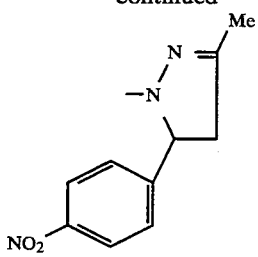 G35
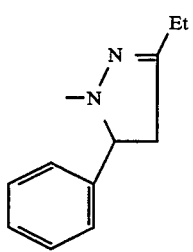 G36
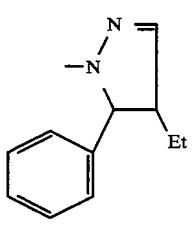 G37
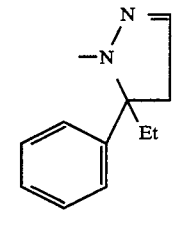 G38
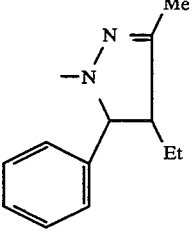 G39
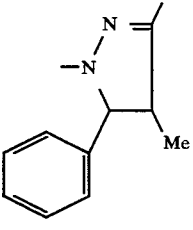 G40
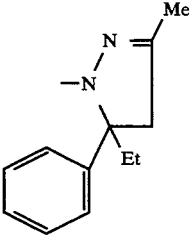 G41
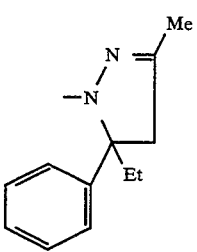 G42
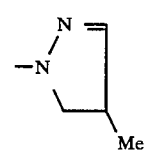 G43
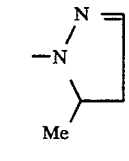 G44
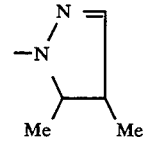 G45
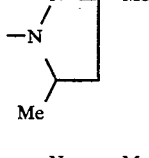 G46
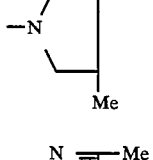 G47
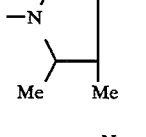 G48
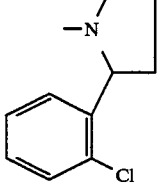 G49
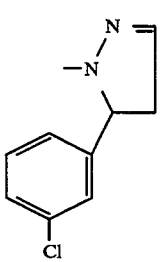 G50

| | |
|---|---|
| 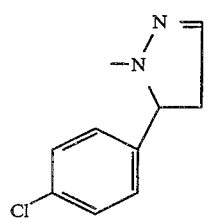 G51 | 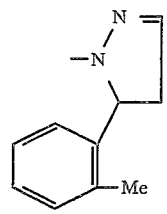 G58 |
| 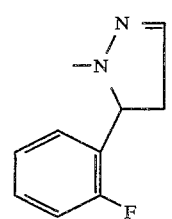 G52 | 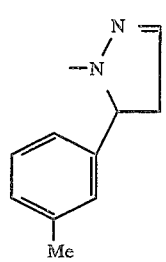 G59 |
| 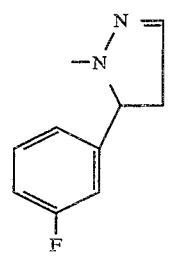 G53 | 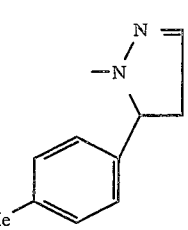 G60 |
| 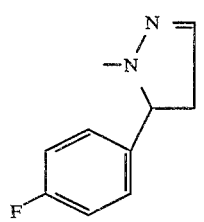 G54 | 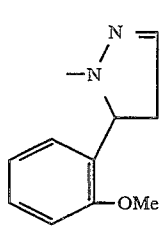 G61 |
| 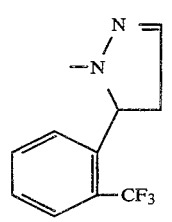 G55 | 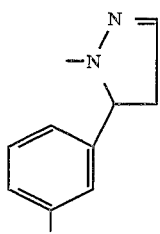 G62 |
| 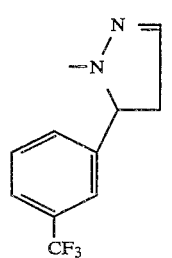 G56 | 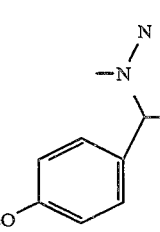 G63 |
| 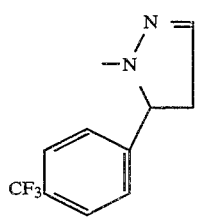 G57 | 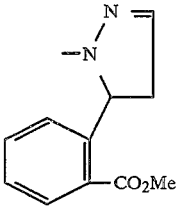 G64 |

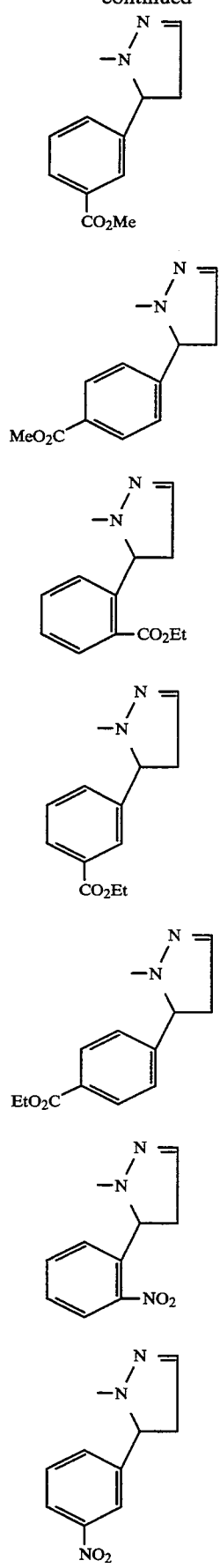
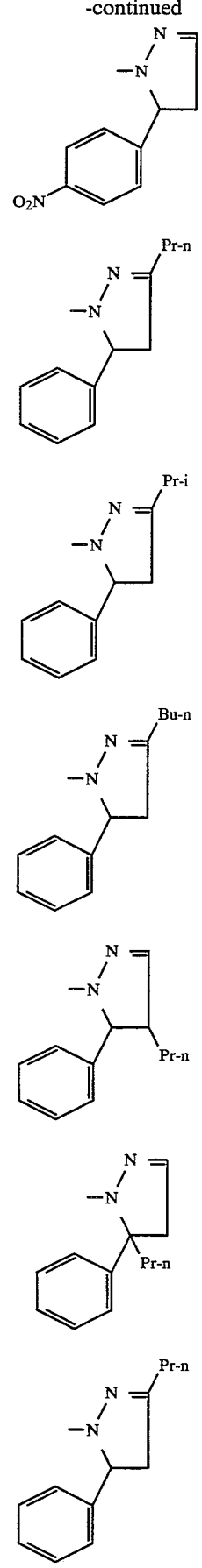

-continued
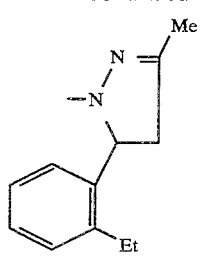 G79
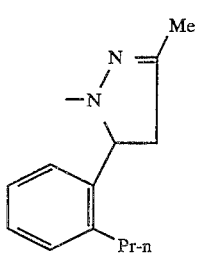 G80
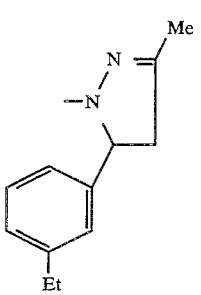 G81
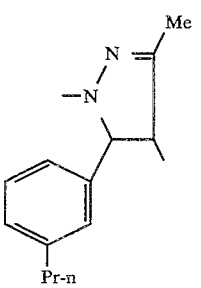 G82
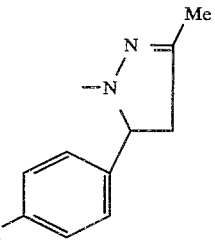 G83
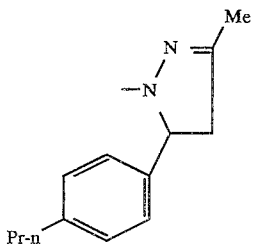 G84
-continued
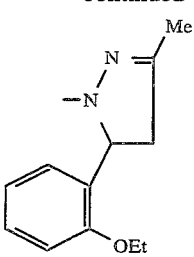 G85
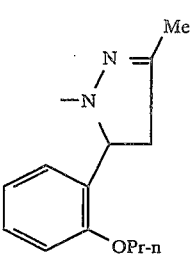 G86
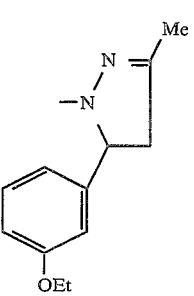 G87
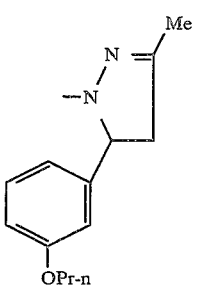 G88
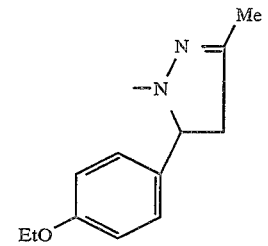 G89
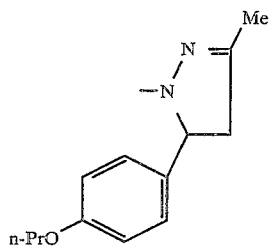 G90

-continued
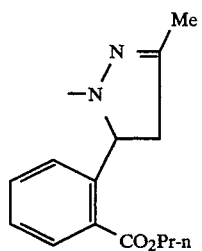 G91
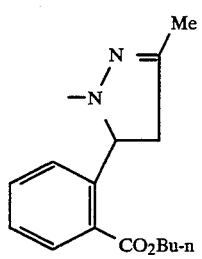 G92
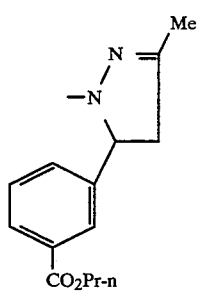 G93
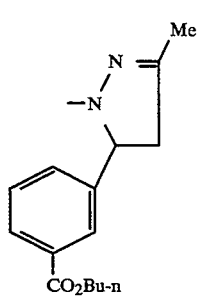 G94
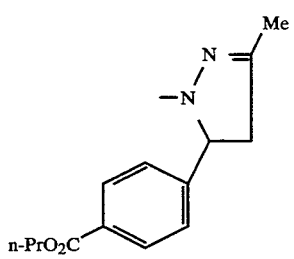 G95
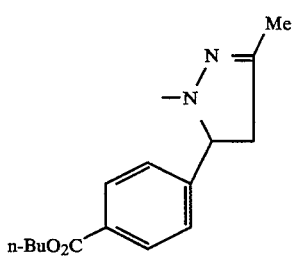 G96
-continued
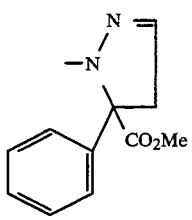 G97
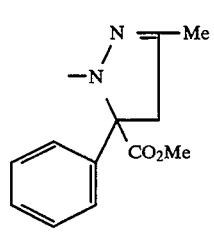 G98
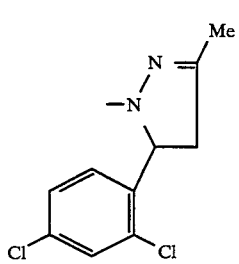 G99
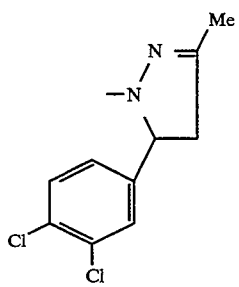 G100
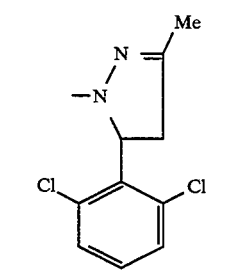 G101
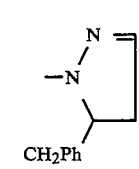 G102
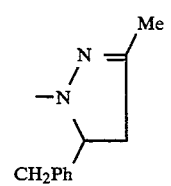 G103

-continued
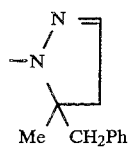 G104
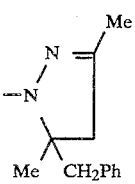 G105
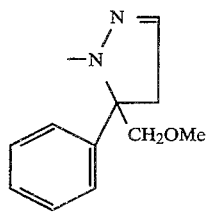 G106
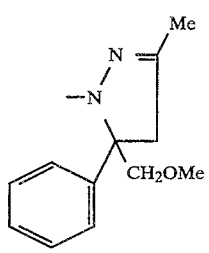 G107
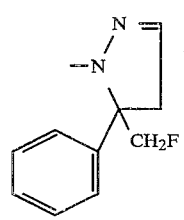 G108
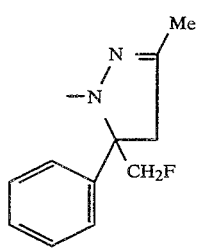 G109
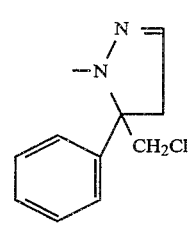 G110
-continued
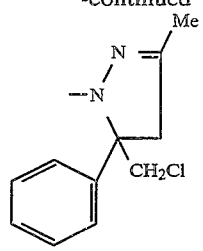 G111
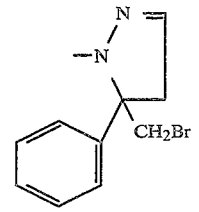 G112
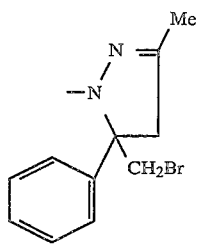 G113
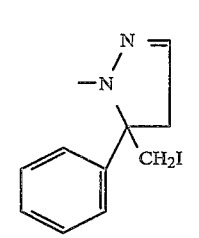 G114
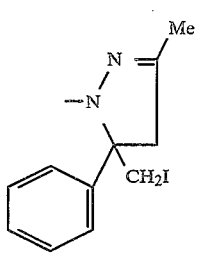 G115
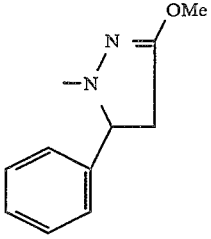 G116
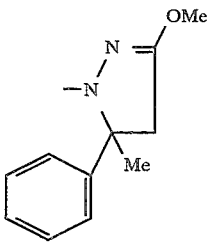 G117

-continued
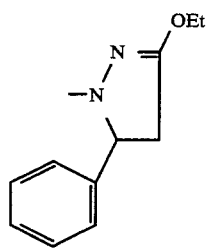 G118
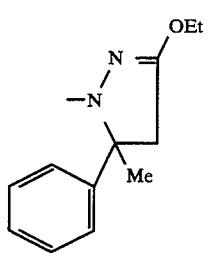 G119
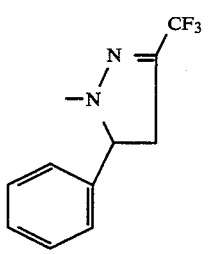 G120
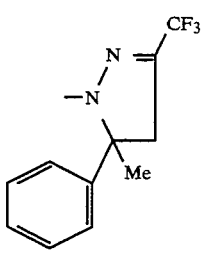 G121
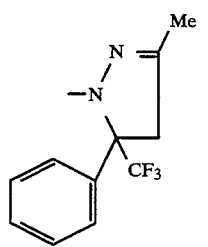 G122
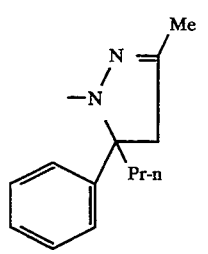 G123
-continued
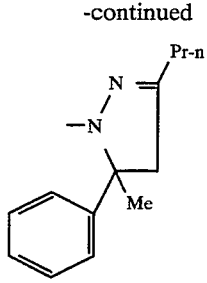 G124
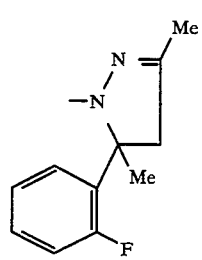 G125
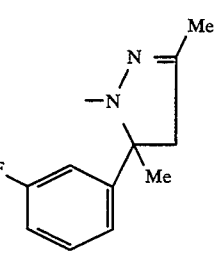 G126
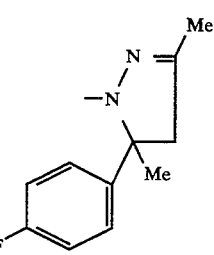 G127
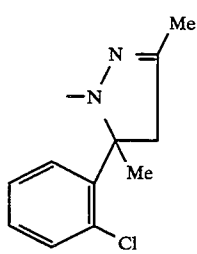 G128
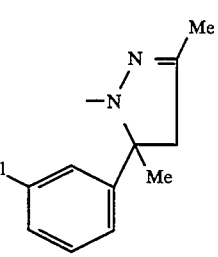 G129

-continued
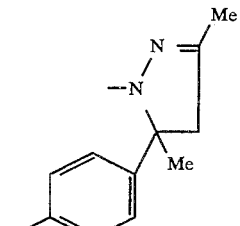 G130
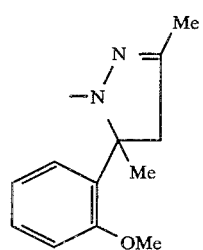 G131
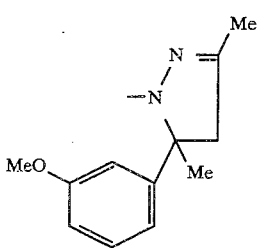 G132
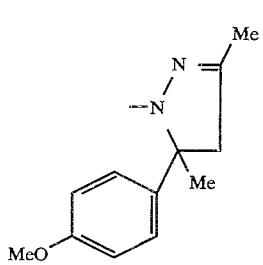 G133
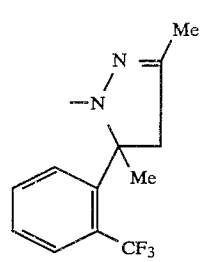 G134
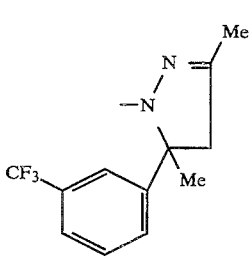 G135
-continued
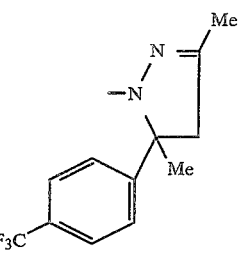 G136
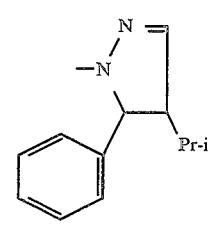 G137
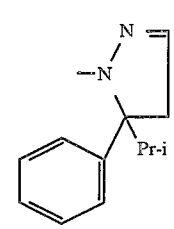 G138
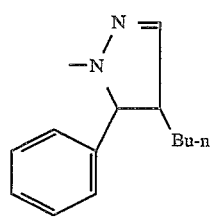 G139
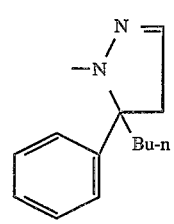 G140
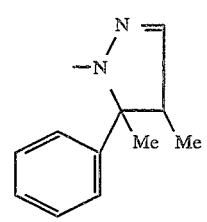 G141
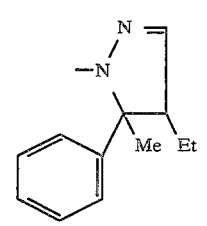 G142

-continued
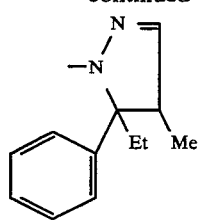 G143
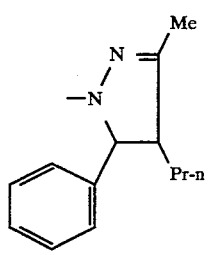 G144
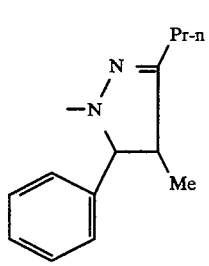 G145
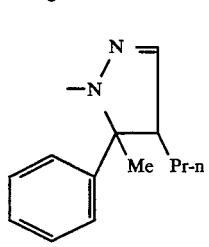 G146
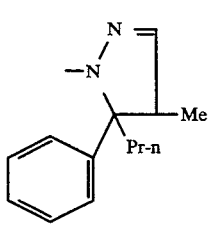 G147
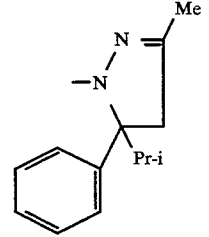 G148
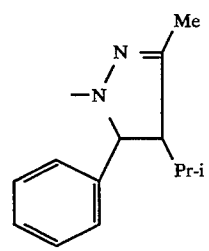 G149
-continued
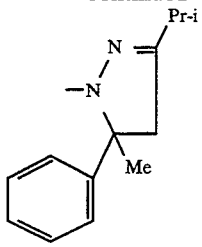 G150
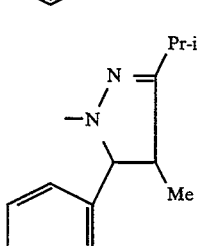 G151
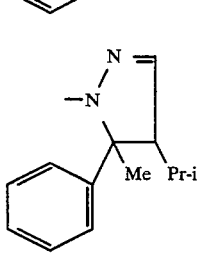 G152
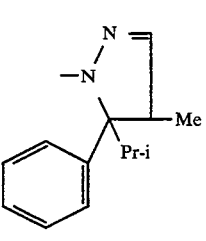 G153
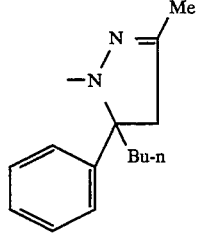 G154
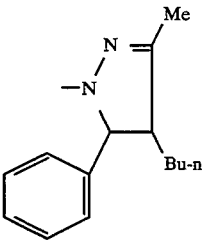 G155
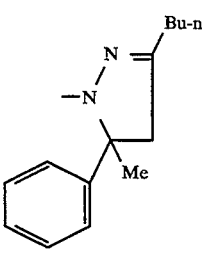 G156

-continued
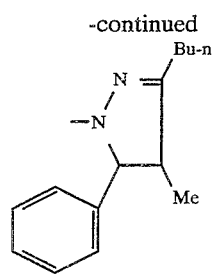 G157
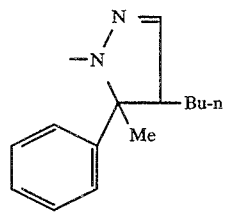 G158
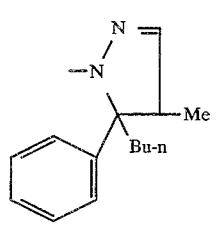 G159
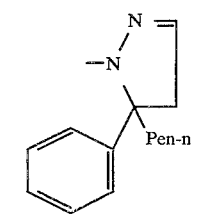 G160
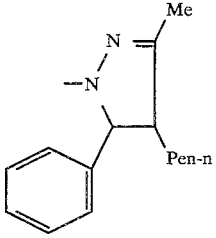 G161
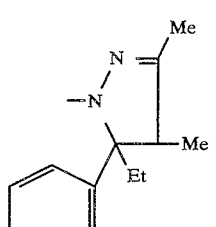 G162
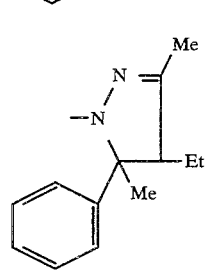 G163
-continued
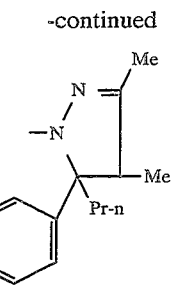 G164
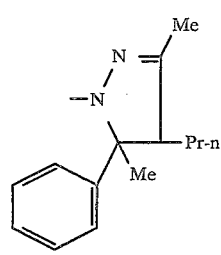 G165
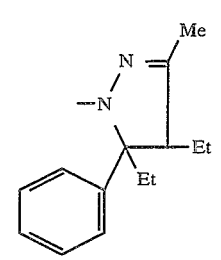 G166
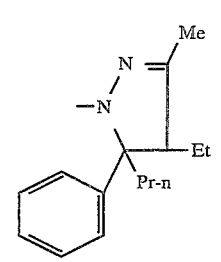 G167
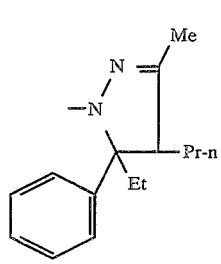 G168
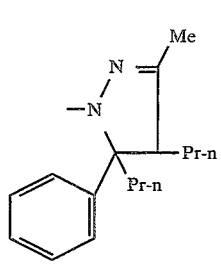 G169

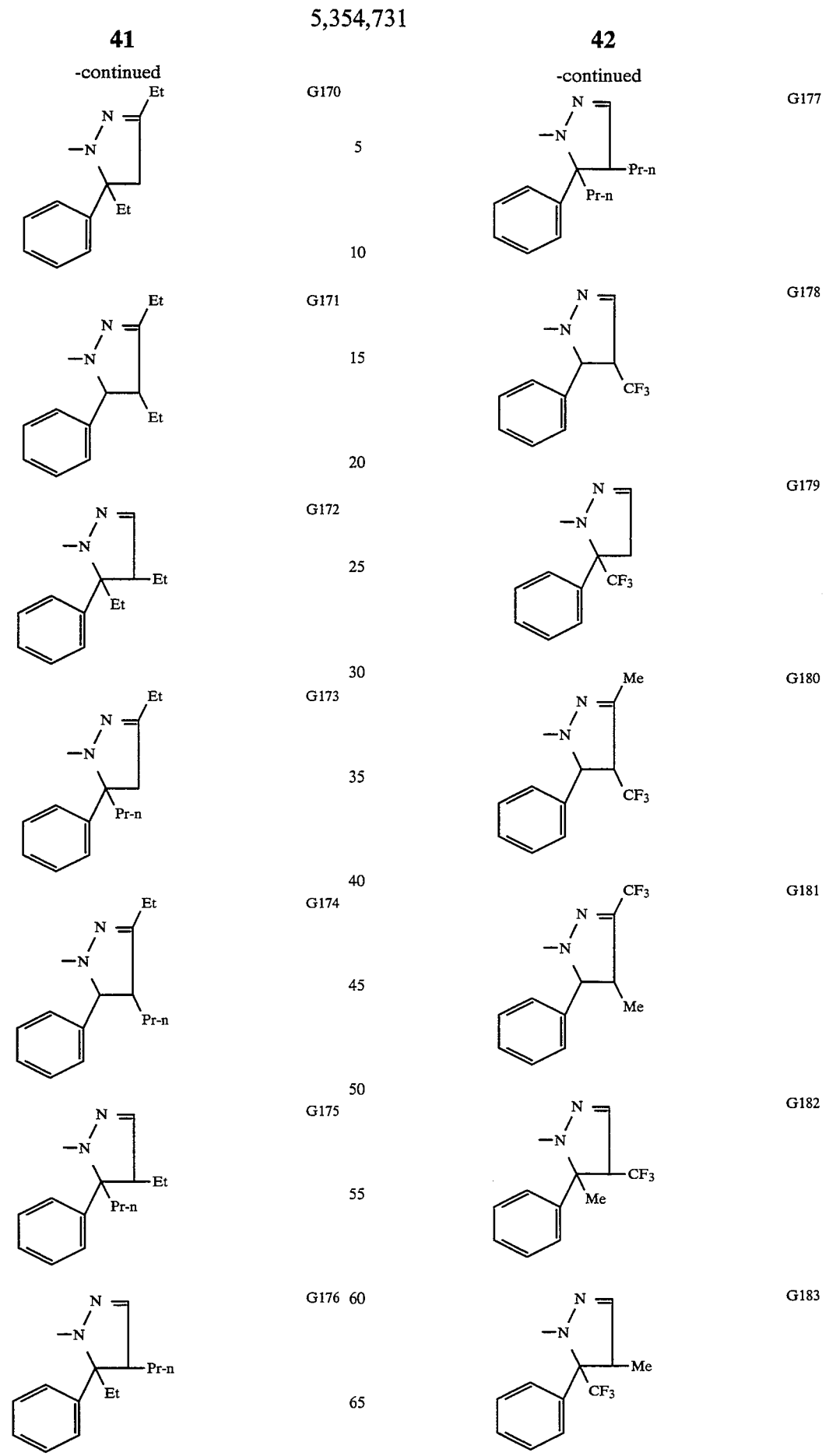

-continued
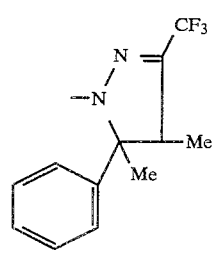 G184
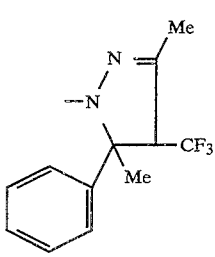 G185
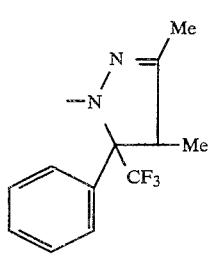 G186
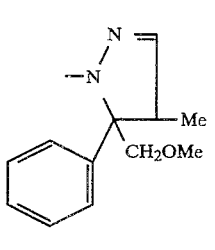 G187
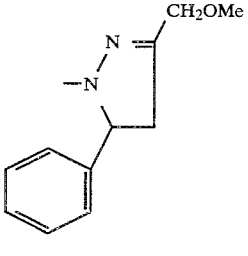 G188
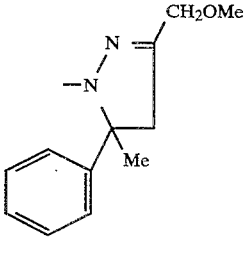 G189
-continued
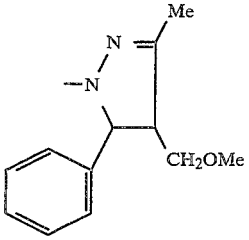 G190
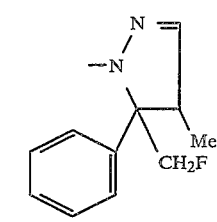 G191
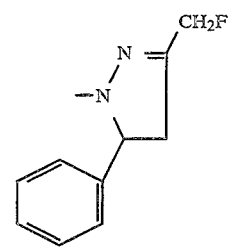 G192
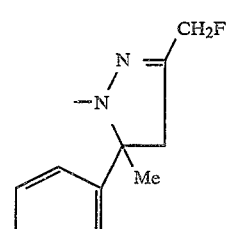 G193
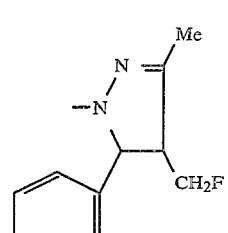 G194
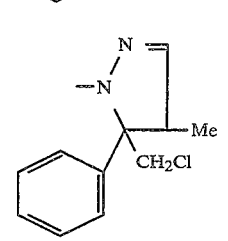 G195
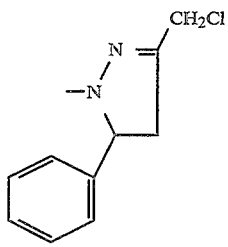 G196

-continued
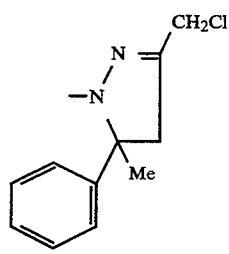 G197
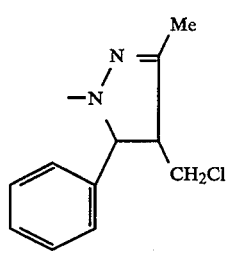 G198
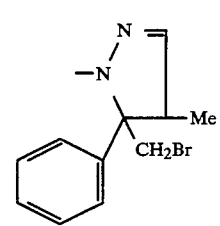 G199
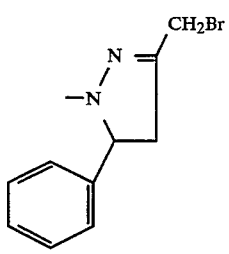 G200
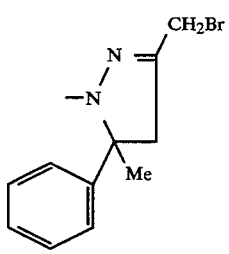 G201
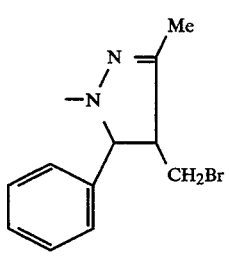 G202
-continued
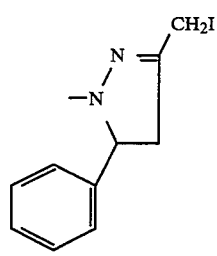 G203
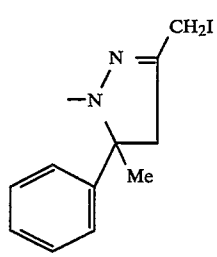 G204
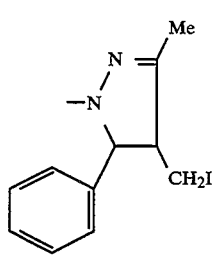 G205
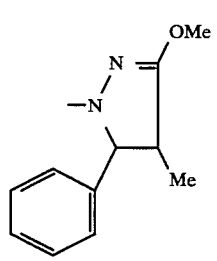 G206
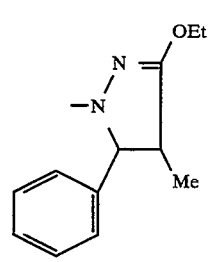 G207
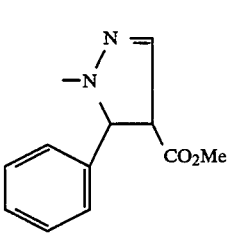 G208

-continued
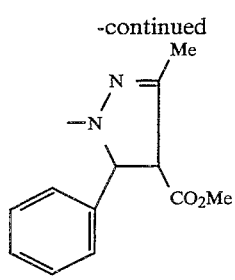 G209
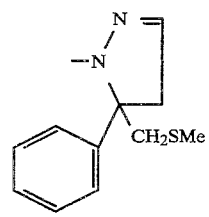 G210
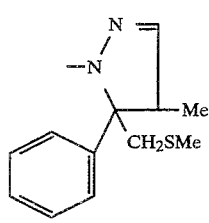 G211
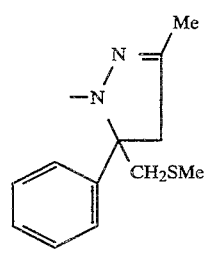 G212
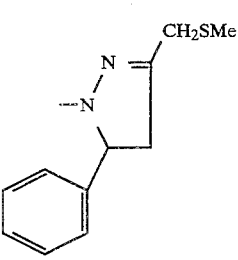 G213
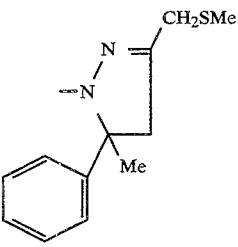 G214
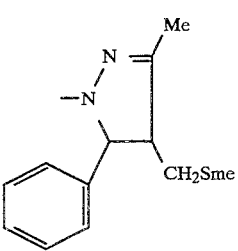 G215
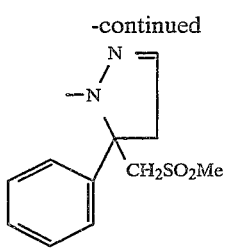 G216
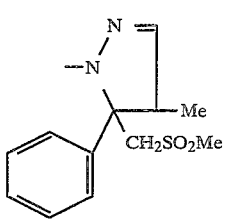 G217
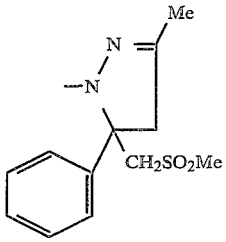 G218
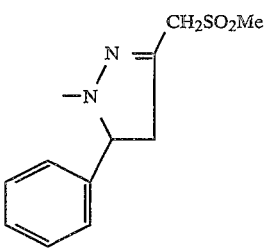 G219
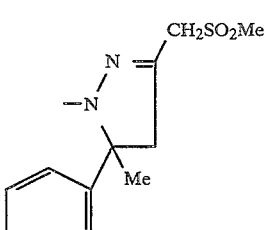 G220
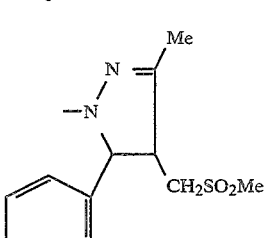 G221
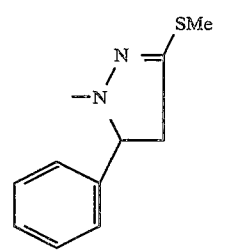 G222

-continued
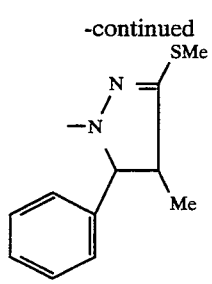 G223
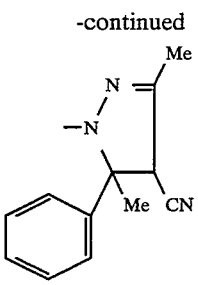 G230
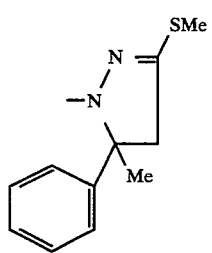 G224
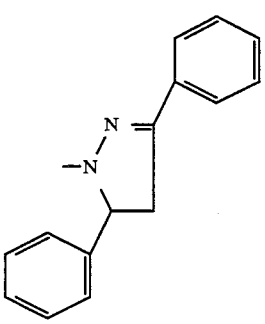 G231
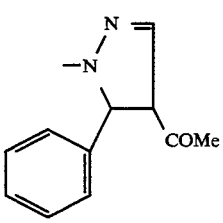 G225
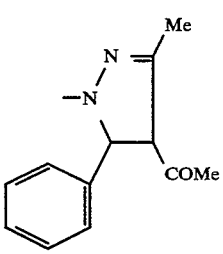 G226
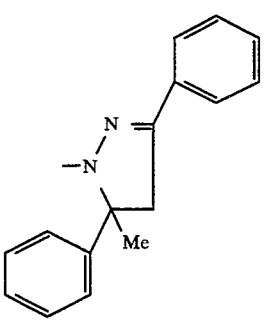 G232
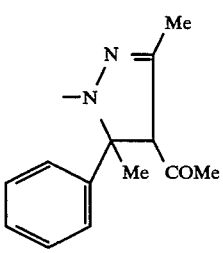 G227
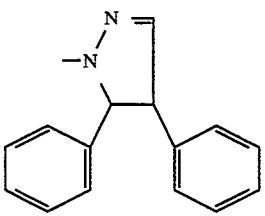 G233
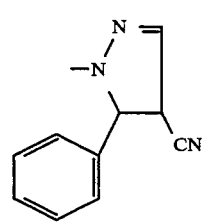 G228
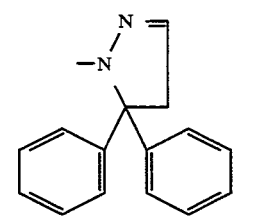 G234
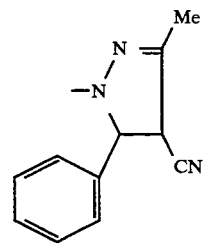 G229
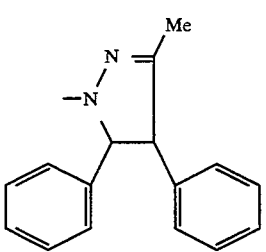 G235

-continued
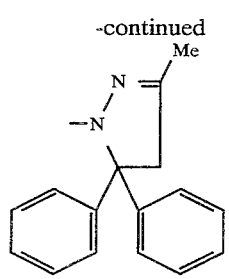 G236
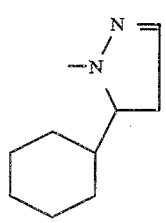 G237
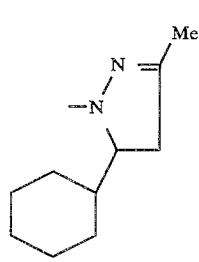 G238
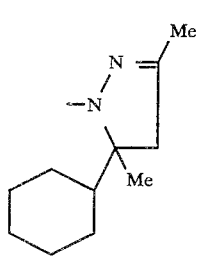 G239
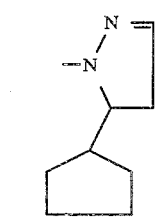 G240
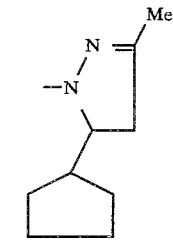 G241
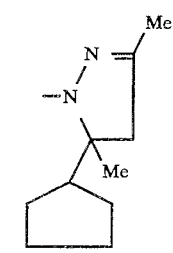 G242
-continued
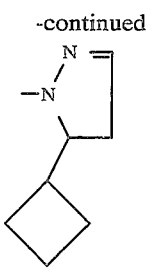 G243
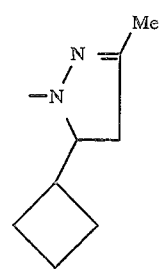 G244
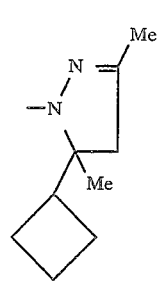 G245
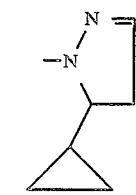 G246
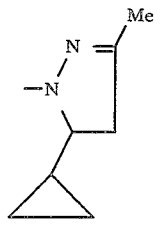 G247
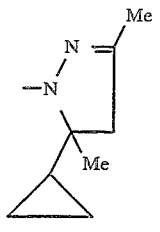 G248
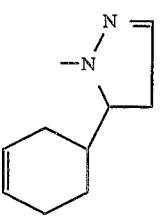 G249

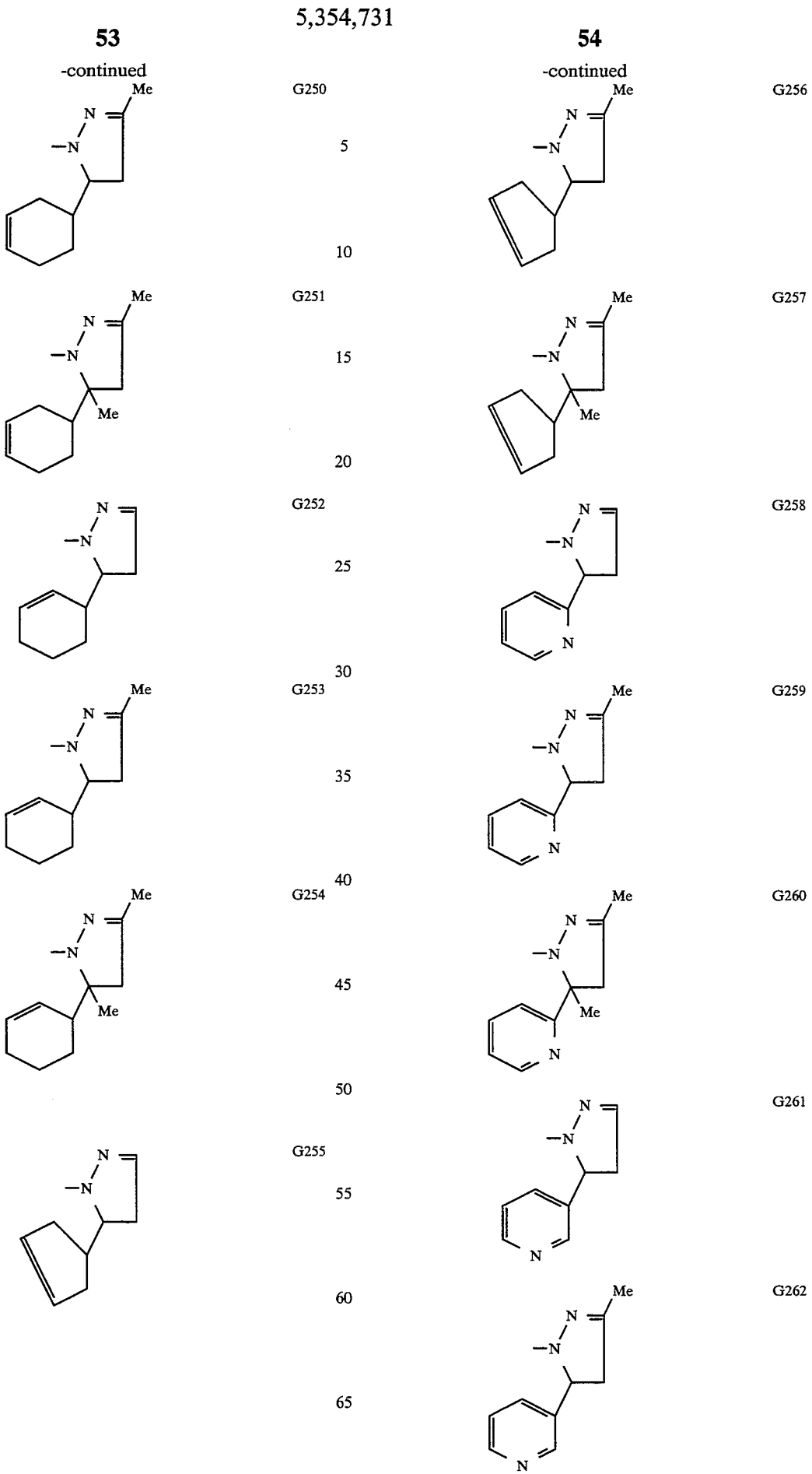

-continued
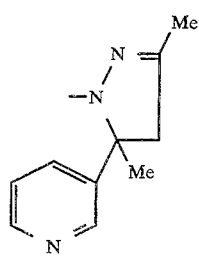 G263
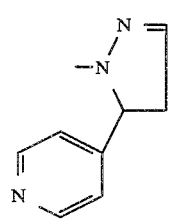 G264
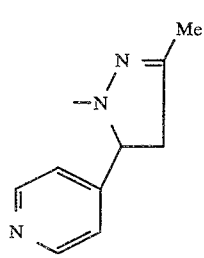 G265
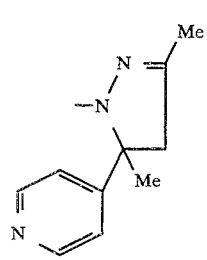 G266
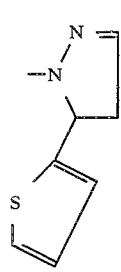 G267
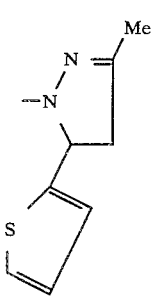 G268
-continued
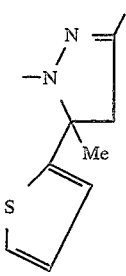 G269
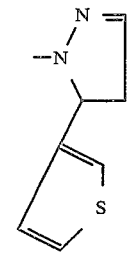 G270
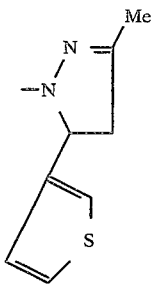 G271
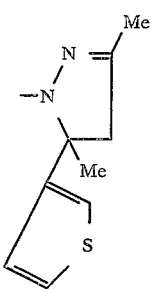 G272
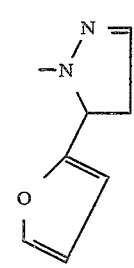 G273
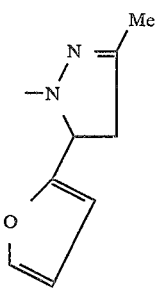 G274

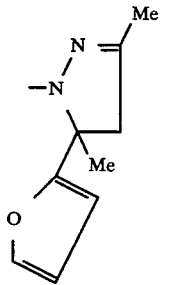 G275
 G276
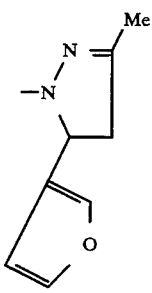 G277
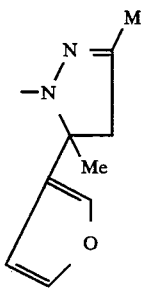 G278
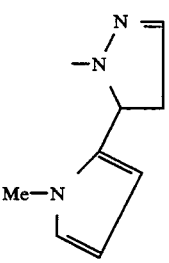 G279
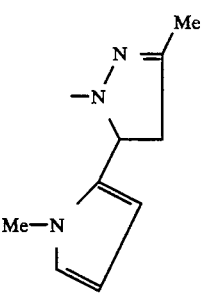 G280
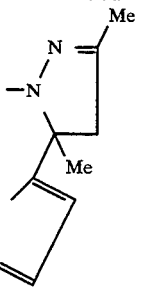 G281
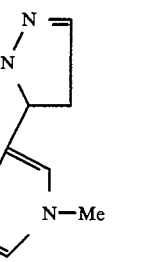 G282
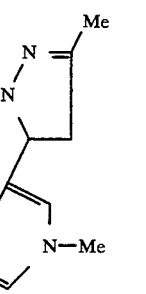 G283
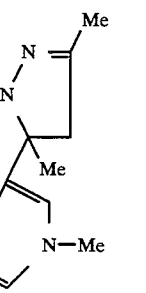 G284
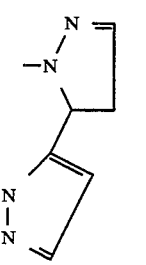 G285
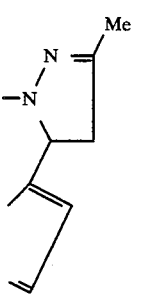 G286

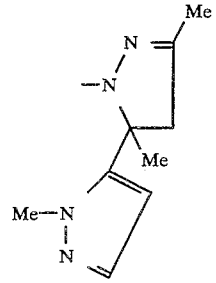 G287
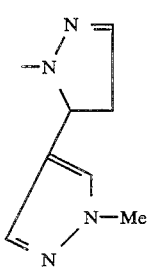 G288
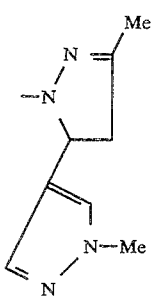 G289
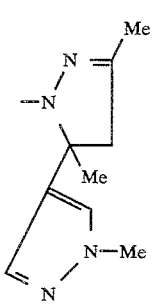 G290
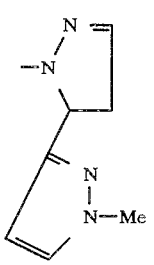 G291
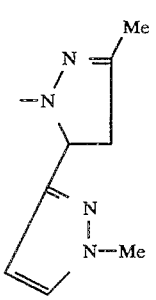 G292
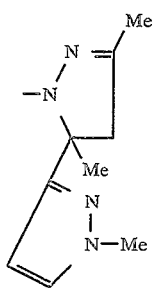 G293
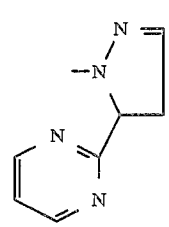 G294
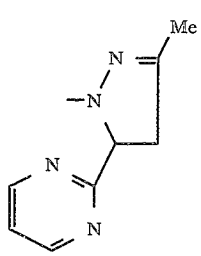 G295
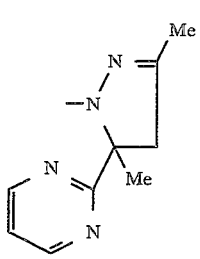 G296
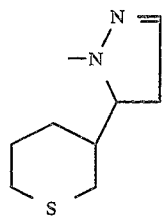 G297
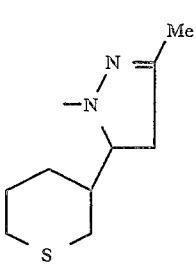 G298

61
-continued
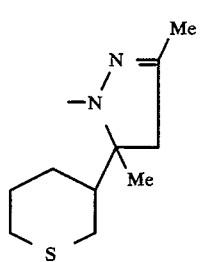 G299
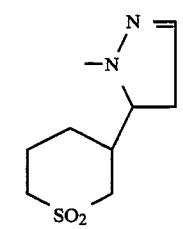 G300
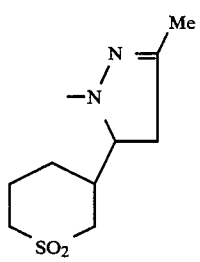 G301
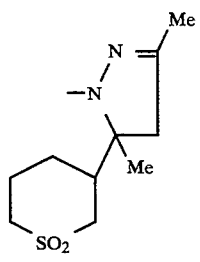 G302
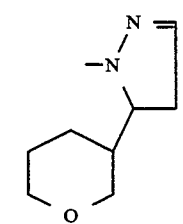 G303
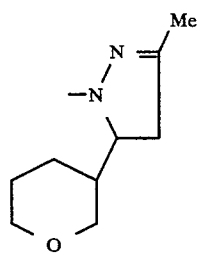 G304
62
-continued
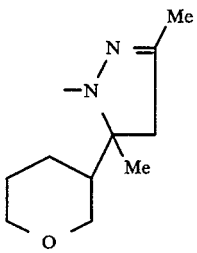 G305
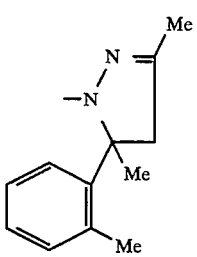 G306
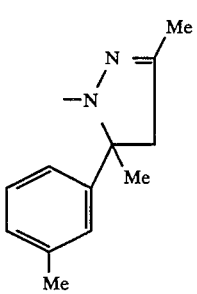 G307
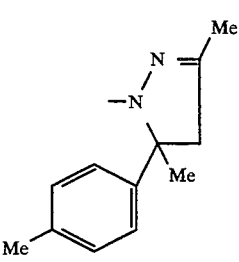 G308
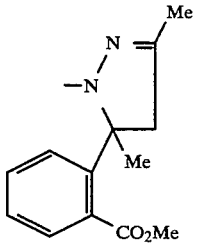 G309
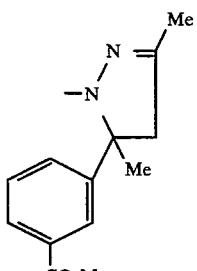 G310

G311 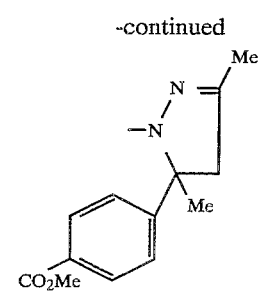
G312 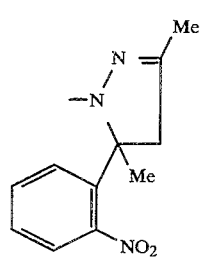
G313 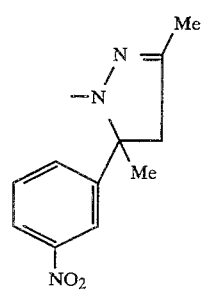
G314 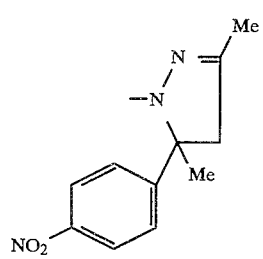
G315 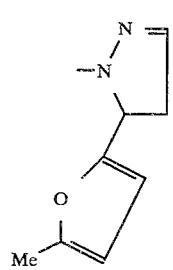
G316 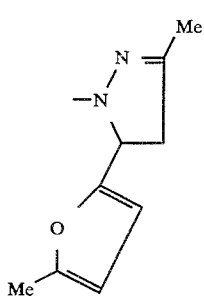
G317 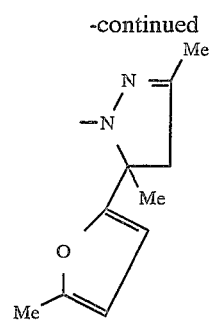
G318 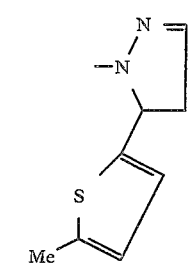
G319 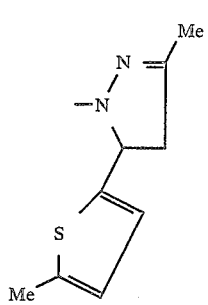
G320 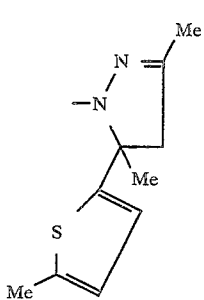
G321 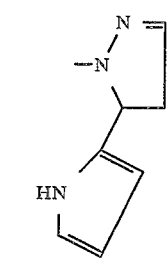
G322 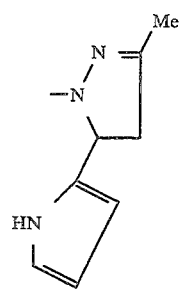

-continued
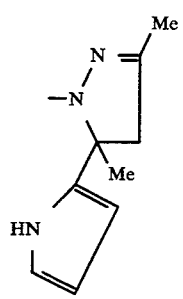
G323
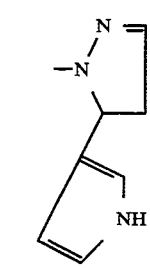
G324
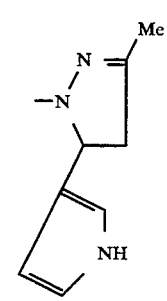
G325
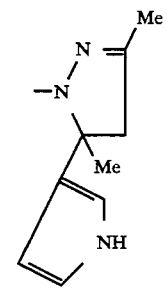
G326
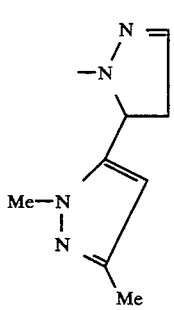
G327
-continued
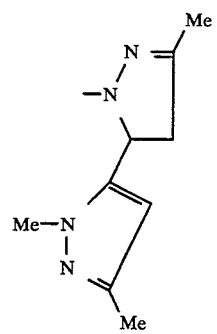
G328
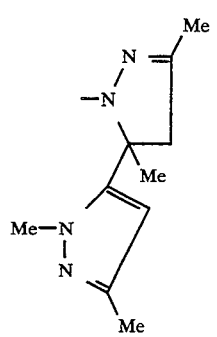
G329
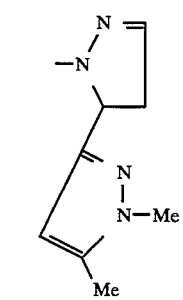
G330
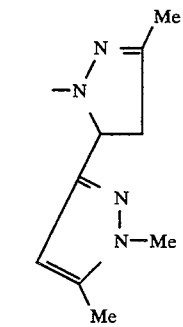
G331
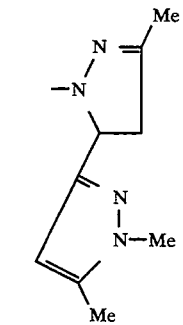
G332

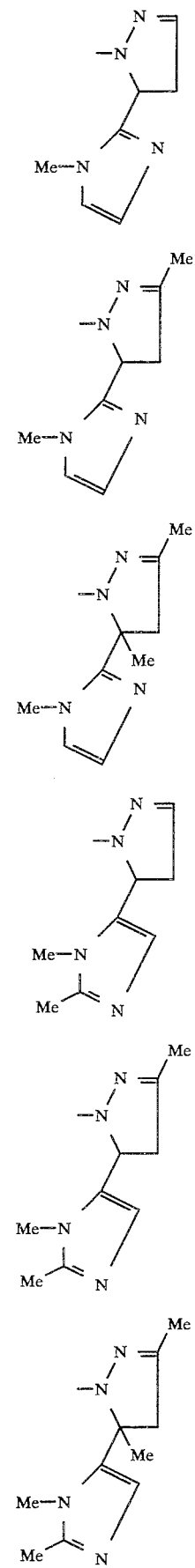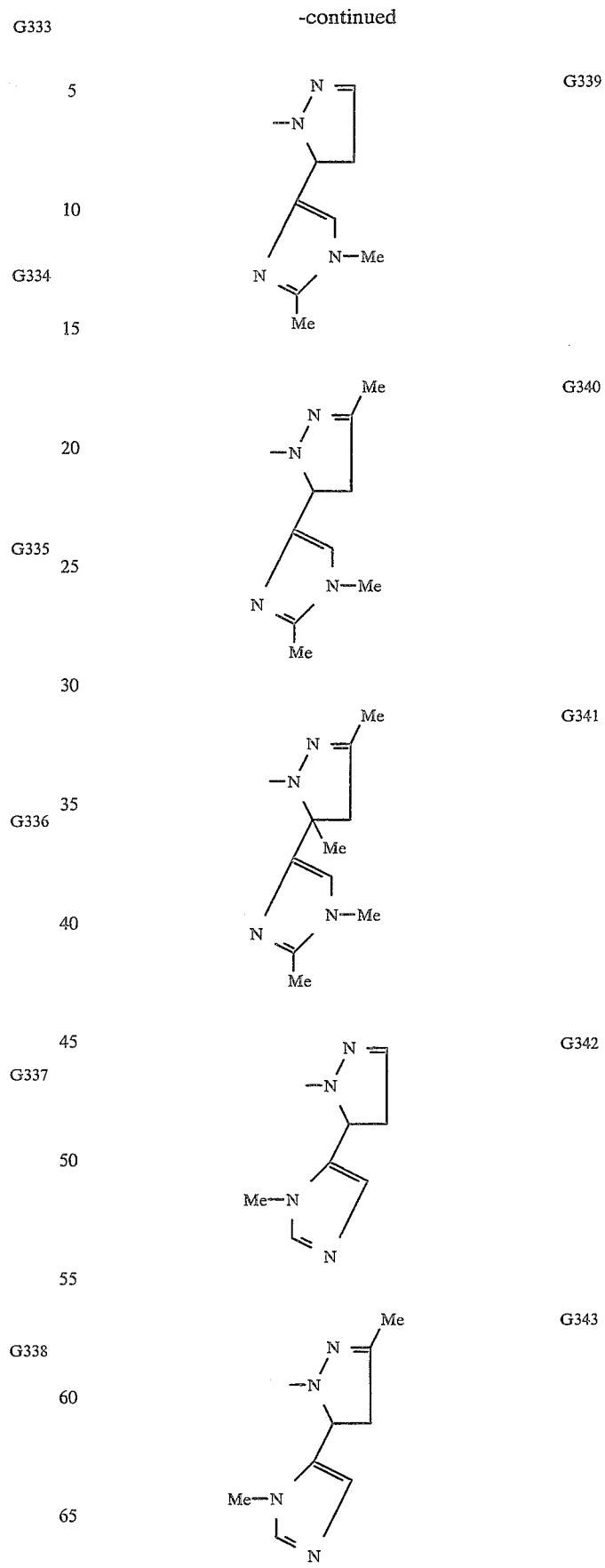

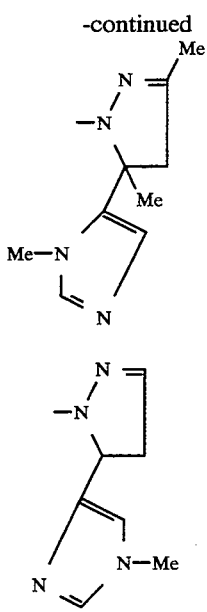 G344
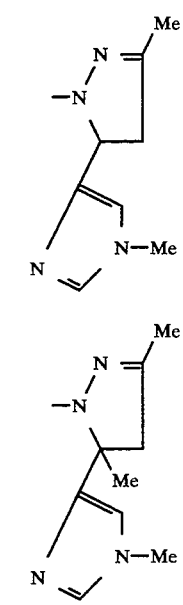 G345
G346
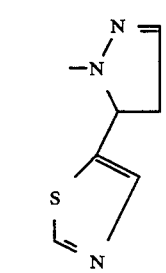 G347
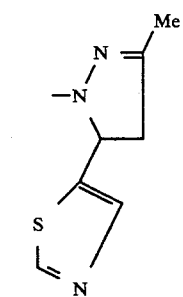 G348
G349
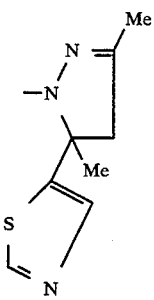 G350
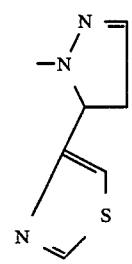 G351
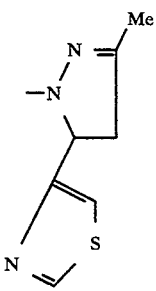 G352
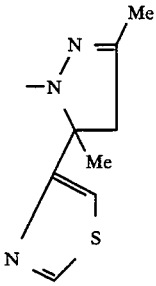 G353
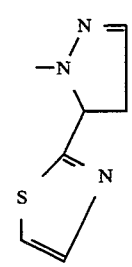 G354
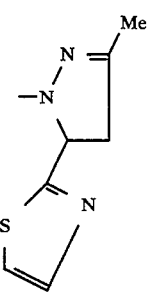 G355

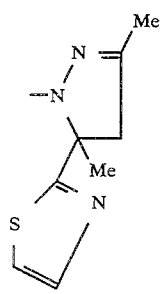 G356
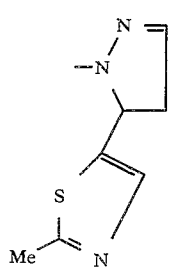 G357
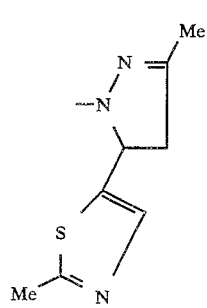 G358
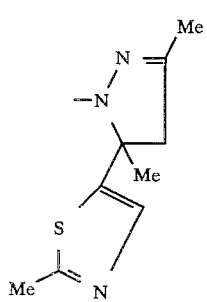 G359
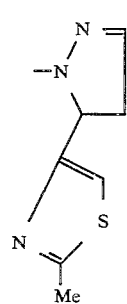 G360
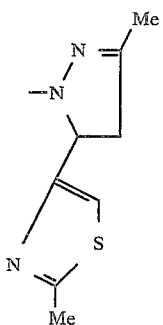 G361
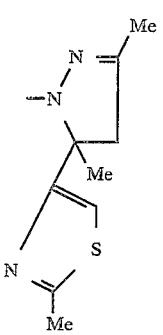 G362
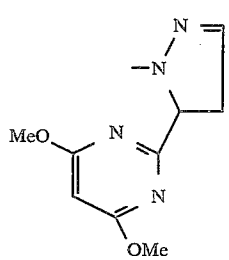 G363
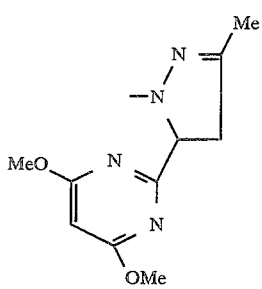 G364
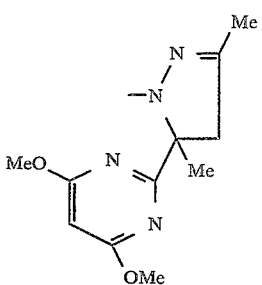 G365

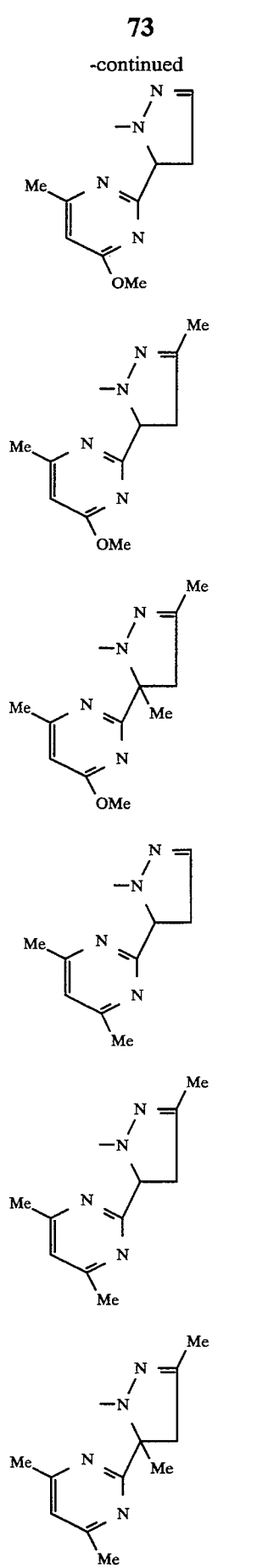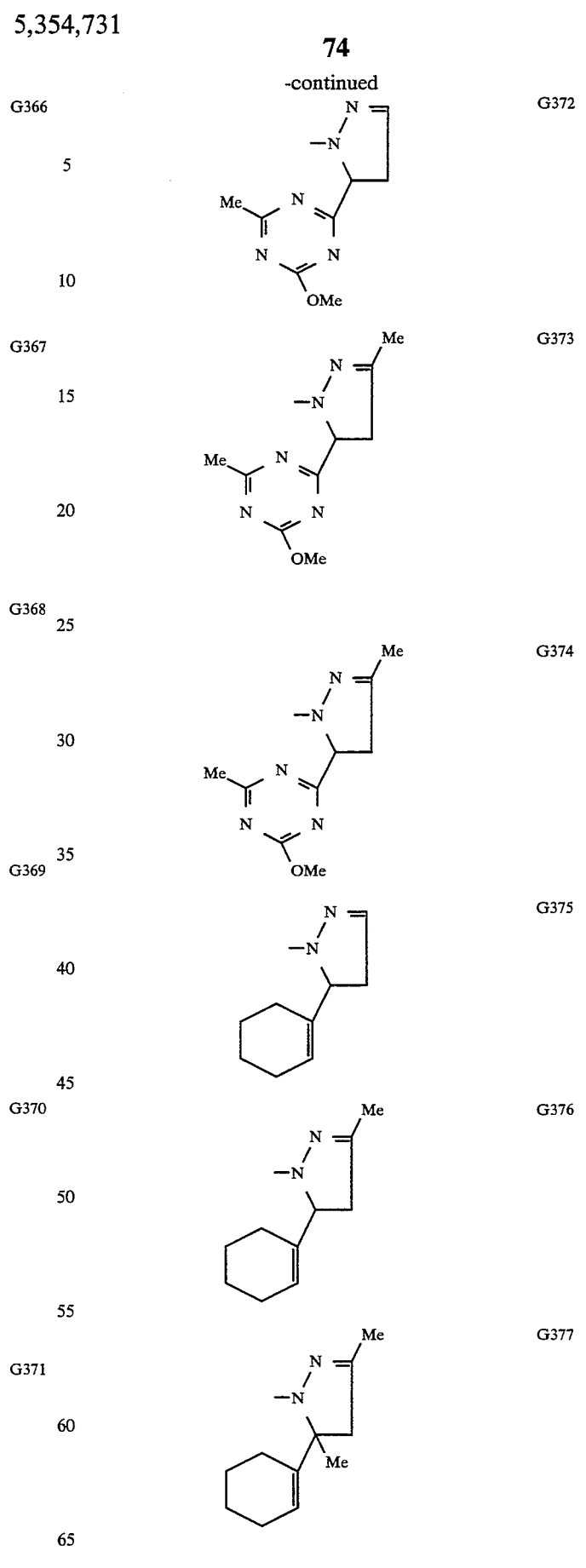

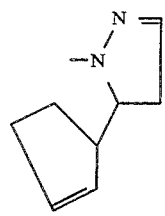 G378
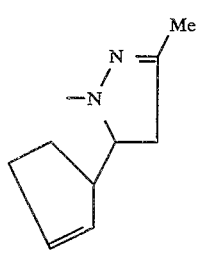 G379
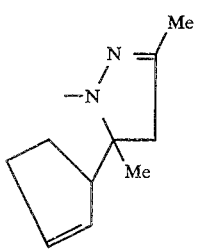 G380
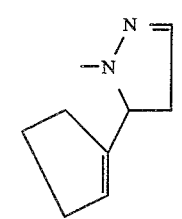 G381
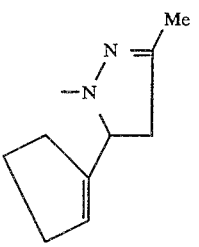 G382
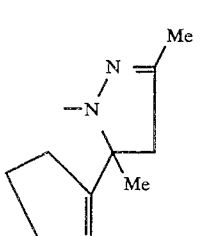 G383
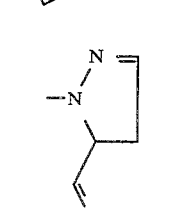 G384
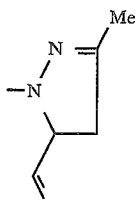 G385
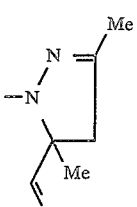 G386
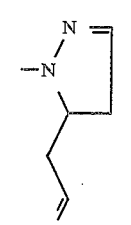 G387
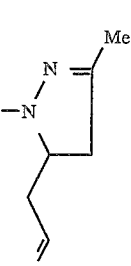 G388
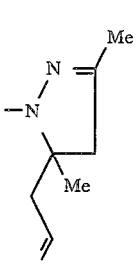 G389
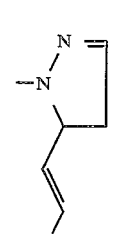 G390
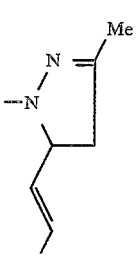 G391

-continued
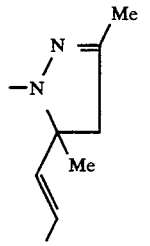 G392
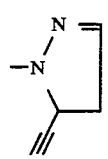 G393
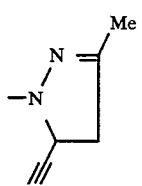 G394
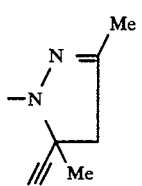 G395
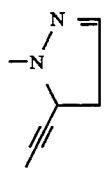 G396
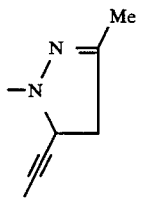 G397
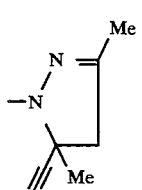 G398
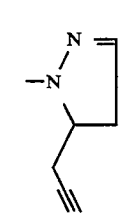 G399
-continued
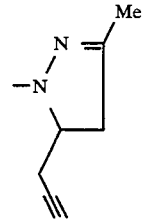 G400
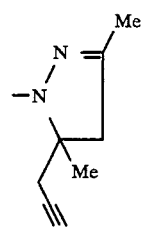 G401
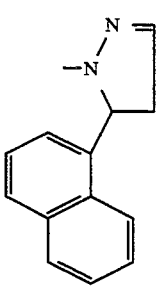 G402
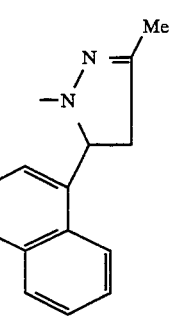 G403
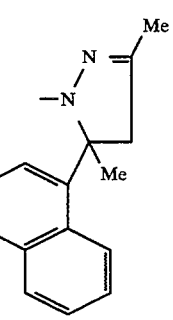 G404
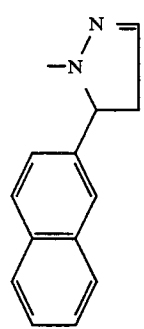 G405

-continued
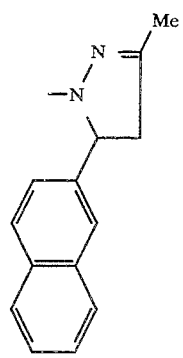 G406
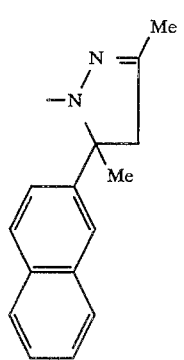 G407
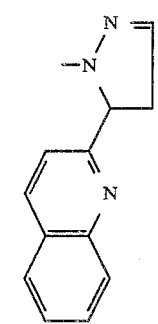 G408
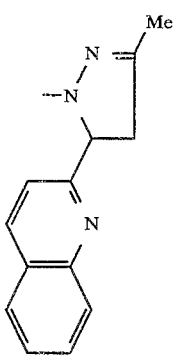 G409
-continued
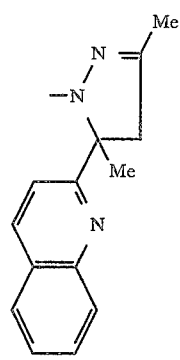 G410
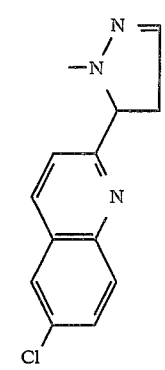 G411
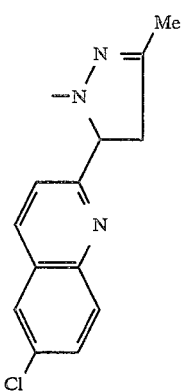 G412
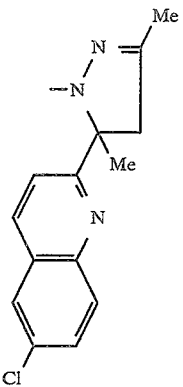 G413

-continued
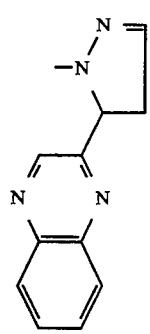 G414
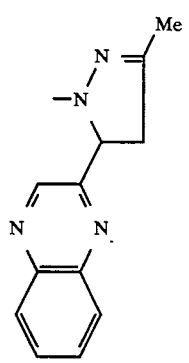 G415
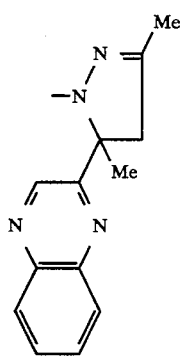 G416
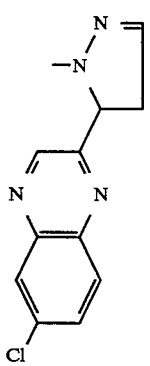 G417
-continued
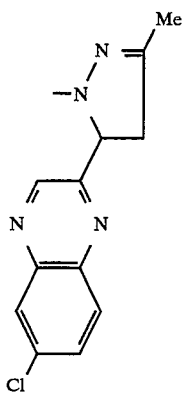 G418
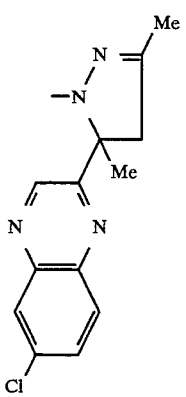 G419
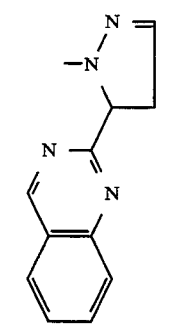 G420
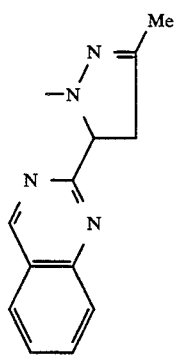 G421

-continued
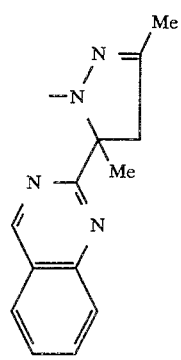
G422
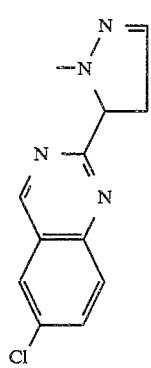
G423
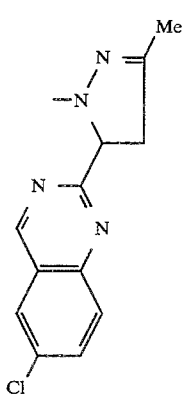
G424
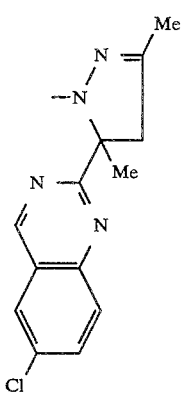
G425
-continued
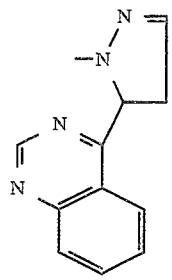
G426
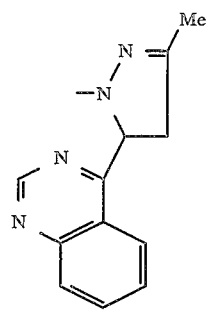
G427
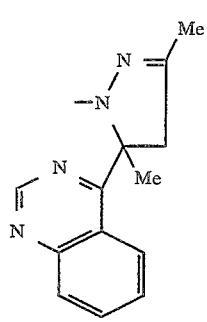
G428
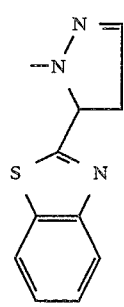
G429
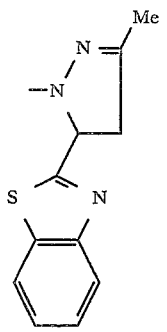
G430

-continued
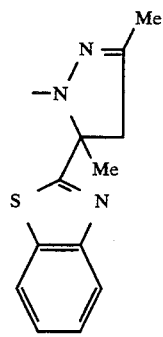 G431
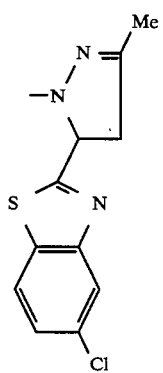 G432
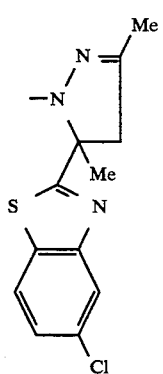 G433
G434
-continued
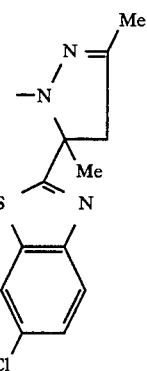 G435
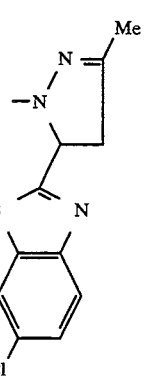 G436
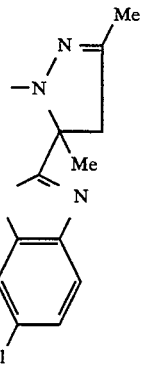 G437
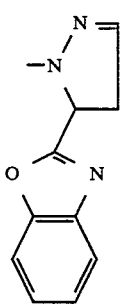 G438

-continued
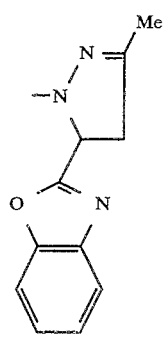 G439
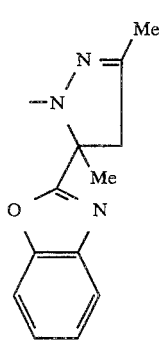 G440
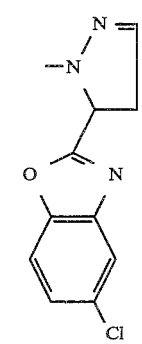 G441
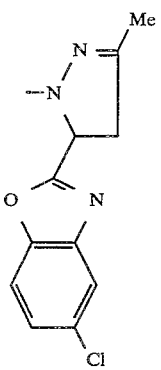 G442
-continued
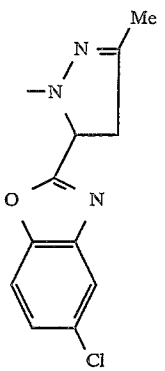 G443
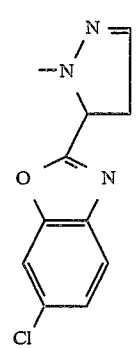 G444
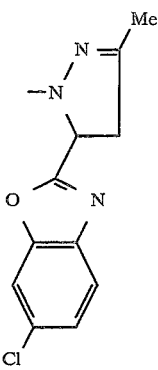 G445
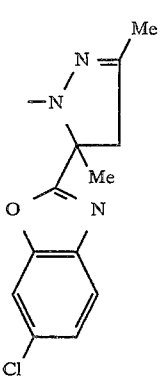 G446

-continued
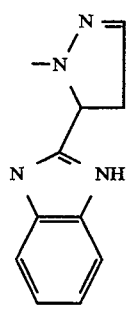 G447
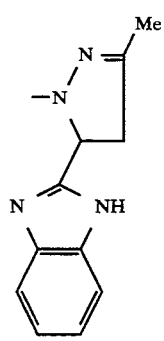 G448
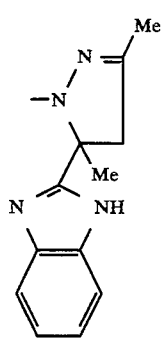 G449
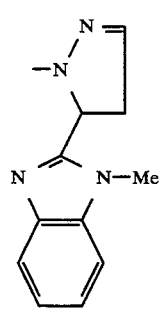 G450
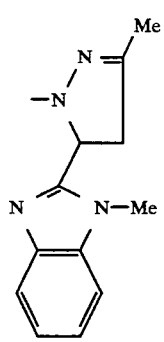 G451
-continued
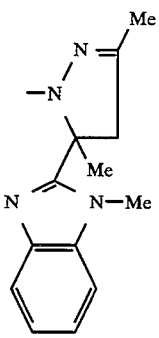 G452
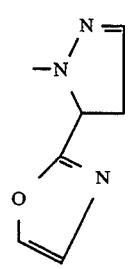 G453
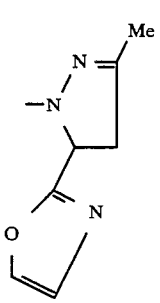 G454
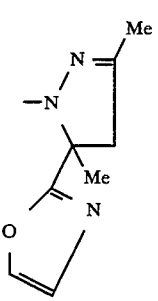 G455
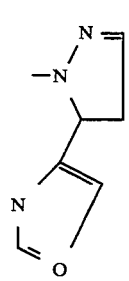 G456

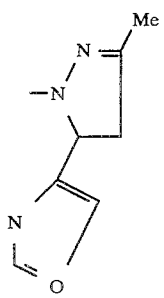 G457
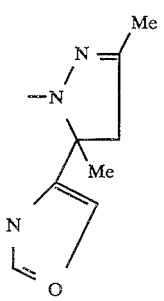 G458
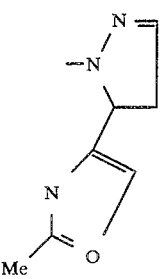 G459
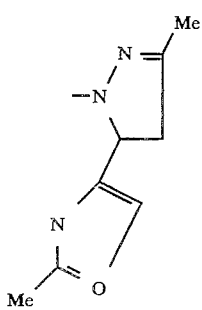 G460
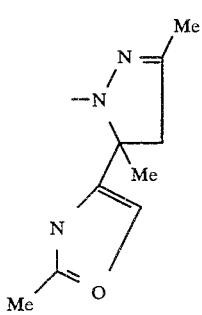 G461
 G462
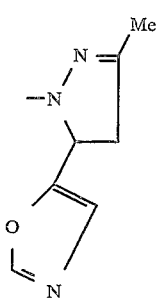 G463
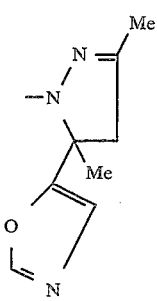 G464
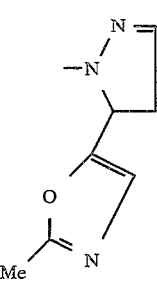 G465
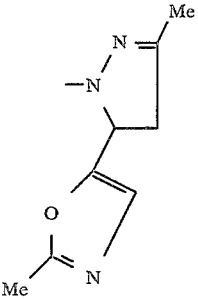 G466

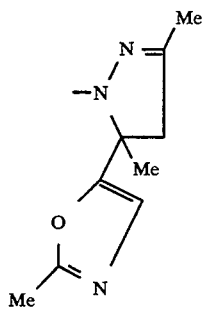 G467
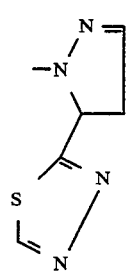 G468
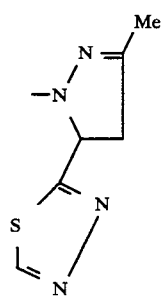 G469
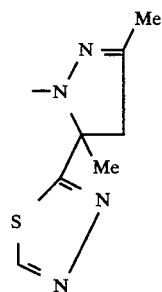 G470
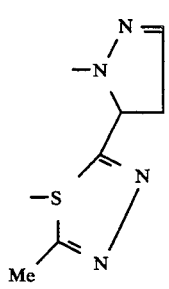 G471
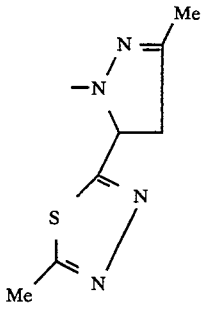 G472
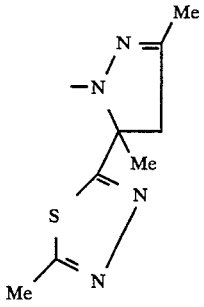 G473
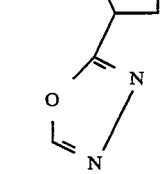 G474
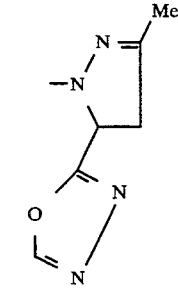 G475
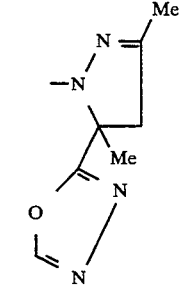 G476

G477 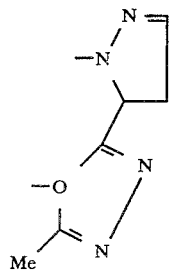

G478 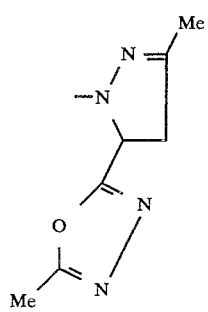

G479 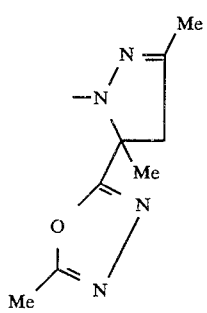

When the compound of the present invention is to be used as a herbicide, it is usually mixed with a suitable carrier, for instance, a solid carrier such as clay, talc, bentonite or diatomaceous earth, or a liquid carrier such as water, an alcohol (such as methanol or ethanol), an aromatic hydrocarbon (such as benzene, toluene or xylene), a chlorinated hydrocarbon, an ether, a ketone, an ester (such as ethyl acetate), or an acid amide (such as N,N-dimethylformamide). If desired, an emulsifier, a dispersing agent, a suspending agent, a penetrating agent, a spreader or a stabilizer may be added to prepare an optional formulation such as a liquid formulation, an emulsifiable concentrate, a wettable powder, a dust, a granule or a flowable.

Now, formulation examples of the herbicides containing the compounds of the present invention as active ingredients, will be given. However, it should be understood that the present invention is by no means restricted to such specific examples. In the following formulation examples, "parts" means "parts by weight".

FORMULATION EXAMPLE 1

Wettable powder

| | |
|---|---|
| Compound No. 1 of the present invention | 20 parts |
| Zeeklite A (tradename for a kaolin-type clay, manufactured by Zeeklite Industries, Co., Ltd.) | 76 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

FORMULATION EXAMPLE 2

Wettable Powder

| | |
|---|---|
| Compound No. 3 of the present invention | 40 parts |
| Zeeklite A (tradename for a kaolin-type clay, manufactured by Zeeklite Industries, Co., Ltd.) | 54 parts |
| Sorpol 5039 (tradename for a mixture of a nonionic surfactant and an anionic surfactant, manufactured by Toho Chemical Industry Co., Ltd.) | 2 parts |
| Carplex (tradename for a coagulation-preventing agent composed of a mixture of a surfactant and fine silica powder, manufactured by Shionogi Pharmaceutical Co., Ltd.) | 4 parts |

The above ingredients are homogeneously pulverized and mixed to form a wettable powder.

FORMULATION EXAMPLE 3

Emulsifiable Concentrate

| | |
|---|---|
| Compound No. 19 of the present invention | 5 parts |
| Xylene | 75 parts |
| N,N-dimethylformamide | 15 parts |
| Sorpol 2680 (tradename for a mixture of a nonionic surfactant and an anionic surfactant, manufactured by Toho Chemical Industry Co., Ltd.) | 5 parts |

The above ingredients are homogeneously mixed to form an emulsifiable concentrate. In its use, the above emulsifiable concentrate is diluted with water from 10 to 10,000 times and applied so that the active ingredient will be from 0.005 to 10 kg per hectare.

FORMULATION EXAMPLE 4

Flowable

| | |
|---|---|
| Compound No. 21 of the present invention | 25 parts |
| Agrizole S-710 (tradename for a nonionic surfactant, manufactured by Kao Corp.) | 10 parts |
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 44.5 parts |

The above ingredients were homogeneously mixed to obtain a flowable.

FORMULATION EXAMPLE 5

Flowable

| | |
|---|---|
| Compound No. 3 of the present invention | 40 parts |
| Agrizole S-710 (tradename for a nonionic surfactant, manufactured by Kao Corp.) | 10 parts |

-continued

| | |
|---|---|
| Runox 1000C (tradename for an anionic surfactant, manufactured by Toho Chemical Industry Co., Ltd.) | 0.5 part |
| 1% Rodopol water (tradename for a thickener, manufactured by Rhone-Poulenc) | 20 parts |
| Water | 29.5 parts |

The above ingredients were homogeneously mixed to obtain a flowable.

FORMULATION EXAMPLE 6

Granule

| | |
|---|---|
| Compound No. 13 of the present invention | 1 part |
| Bentonite | 55 parts |
| Talc | 44 parts |

The above ingredients were homogeneously mixed and pulverized, and after an addition of a small amount of water, the mixture was stirred, mixed and granulated by an extrusion-type granulating machine, followed by drying to obtain a granule.

Further, the compound of the present invention may be combined with other herbicides, various insecticides, fungicides and synergism agents at the time of the preparation of the formulations or at the time of the application, as the case requires.

As such other herbicides, compound disclosed in Farm Chemicals Handbook (1989) may, for example, be mentioned.

The compound of the present invention can be applied to control various weeds not only in the agricultural and horticultural fields such as upland fields, paddy fields or orchards, but also in non-agricultural fields such as play grounds, non-used vacant fields or railway sides.

The dose varies depending upon the application site, the season for application, the manner of application, the type of weeds to be controlled, the type of crop plants, etc. However, the dose is usually within a range of from 0.005 to 10 kg per hectare as the amount of the active ingredient.

Now, the herbicidal activities of the compounds of the present invention will be described in detail with reference to the following test examples. The compound nos. referred to in the test examples correspond to the compound nos. given above.

TEST EXAMPLE 1

Test on the Herbicidal Effects in Soil Treatment

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliata, Rorippa indica, Oryza sativa, Zea mays, Triticum aestivum, Glycine max* and *Gossypium herbaceum* were sown, and the soil was covered thereon in the thickness of about 1.5 cm, and then a herbicide solution was applied onto the surface of the soil uniformly so that the active ingredient was distributed at a predetermined concentration. The herbicide solution was prepared by diluting the wettable powder as described in the foregoing Formulation Examples with water and applied onto the entire soil surface by means of a small spray. Four weeks after the application of the herbicidal solution, the herbicidal effects against each weed and the phytotoxicities against each crop plant were determined on the basis of the following standard ratings. The results are shown in Table 2. (compound nos. correspond to compound nos. in the examples.) Some of the compounds of the present invention exhibit selectivity for certain crop plants.

STANDARD RATINGS

5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

$$\text{Growth control rate (\%)} = \left(1 - \frac{T}{N}\right) \times 100$$

where
T: Weight of the weed grown above the soil surface of the treated area
N: Weight of the weed grown above the soil surface of the non-treated area

TEST EXAMPLE 2

Test on the Herbicidal Effects in Foliage Treatment

A plastic box having a length of 15 cm, a width of 22 cm and a depth of 6 cm was filled with a sterilized diluvial soil, and seeds of *Echinochloa crus-galli, Digitaria adscendens, Cyperus microiria, Solanum nigrum, Galinsoga ciliata, Rorippa indica, Oryza sativa, Zea mays, Triticum aestivum, Glycine max, Gossypium herbaceum* and *Beta vulgaris* were spot-wisely sown, and the soil was covered thereon in a thickness of about 1.5 cm. When the various weeds and crop plants grew to the 2 or 3 leaf stage, a herbicidal solution was uniformly sprayed on the foliages so that the active ingredient was applied in a predetermined concentration.

The herbicidal solution was prepared by diluting the wettable powder as described in the above Formulation Examples with water and applied onto the entire surface of the foliages of the weeds and the crop plants by a small spray. Four weeks after the application of the herbicide solution, the herbicidal effects against each weed and the phytotoxicities against each crop plant were determined on the basis of the standard ratings described in Test Example 1. The results are shown in Table 3. (compound nos. correspond to compound nos. in the examples. )

TEST EXAMPLE 3

Test on the Phytotoxicity Against *Triticum aestivum*

A plastic box having a length of 15 cm, a width of 22 cm and a depth of 6 cm was filled with a sterilized diluvial soil, and seeds of *Triticum aestivum, Avena fatua* and *Alopecurus myosuroides* were spot-wisely sown, and the soil was covered thereon in a thickness of 1 cm.

When the plants grew to 2 or 3 leaf stage, a herbicidal solution was uniformly sprayed on the foliages so that the active ingredient-was applied in a predetermined concentration by a small spray. Twenty days after the treatment, the herbicidal effects against weeds and the phytotoxicity against *Triticum aestivum* were determined on the basis of the standard ratings described in Test Example 1. The results are shown in Table 4. (Compound Nos. correspond to Compound Nos. in the Examples.)

In Tables 2, 3 and 4, the following abbreviations are used.
Dose: Dose of active ingredient
EC: *Echinochloa crus-galli* (barnyardgrass)
DI: *Digitaria adscendens* (large crabgrass)
CY: *Cyperus microiria* (annual sedge)
SO: *Solanum nigrum* (black nightshade)
GA: *Galinsoga ciliata* (hairy galinsoga)
RO: *Rorippa indica* (fieldcress)
OR: *Oryza sativa* (rice)
ZE: *Zea mays* (corn)
TR: *Triticum aestivum* (wheat)
GL: *Glycine max* (soybean)
GO: *Gossypium herbaceum* (cotton)
BE: *Beta vulgaris* (sugar beet)
AV: *Avena fatua* (wild oat)
AL: *Alopecurus myosuroides* (blackgrass)

TABLE 2

| Comp. No. | Dose kg/ha | EC | DI | CY | SO | GA | RO | OR | ZE | TR | GL | GO |
|---|---|---|---|---|---|---|---|---|---|---|---|---|
| 1 | 0.16 | 3 | 4 | 2 | 5 | 5 | 5 | 5 | 1 | 2 | 1 | 1 |
|   | 0.32 | 4 | 5 | 4 | 5 | 5 | 5 | 5 | 2 | 3 | 2 | 3 |
|   | 0.63 | 5 | 5 | 5 | 5 | 5 | 5 | 5 | 3 | 4 | 3 | 4 |
| 3 | 0.16 | 2 | 3 | 3 | 4 | 5 | 5 | 3 | 0 | 0 | 1 | 2 |
|   | 0.32 | 3 | 4 | 4 | 5 | 5 | 5 | 4 | 0 | 1 | 2 | 3 |
|   | 0.63 | 4 | 5 | 5 | 5 | 5 | 5 | 5 | 0 | 2 | 4 | 4 |
| 4 | 0.63 | 3 | 4 | 3 | 5 | 5 | 5 | 4 | 0 | 2 | 1 | 1 |
| 5 | 0.63 | 4 | 5 | 3 | 4 | 5 | 5 | 5 | 1 | 0 | 1 | 2 |
| 7 | 0.16 | 1 | 2 | 1 | 5 | 5 | 5 | 4 | 0 | 0 | 0 | 0 |
|   | 0.32 | 2 | 3 | 2 | 5 | 5 | 5 | 5 | 0 | 0 | 0 | 1 |
|   | 0.63 | 3 | 4 | 4 | 5 | 5 | 5 | 5 | 1 | 1 | 1 | 2 |
| 8 | 0.63 | 3 | 5 | 4 | 5 | 5 | 5 | 4 | 1 | 0 | 2 | 1 |
| 13 | 0.16 | 1 | 1 | 2 | 5 | 5 | 5 | 2 | 0 | 0 | 0 | 1 |
|   | 0.32 | 2 | 2 | 3 | 5 | 5 | 5 | 3 | 0 | 1 | 1 | 2 |
|   | 0.63 | 3 | 4 | 4 | 5 | 5 | 5 | 4 | 0 | 2 | 2 | 3 |
| 19 | 0.63 | 3 | 2 | 3 | 5 | 5 | 5 | 0 | 0 | 0 | 1 | 1 |
| 20 | 0.63 | 2 | 1 | 1 | 4 | 5 | 5 | 0 | 2 | 1 | 2 | 1 |
| 21 | 0.63 | 2 | 1 | 1 | 5 | 5 | 5 | 4 | 1 | 3 | 3 | 3 |
| 28 | 1.6 | 3 | 4 | 4 | 4 | 5 | 5 | 4 | 1 | 1 | 2 | 2 |
|   | 3.2 | 4 | 5 | 5 | 5 | 5 | 5 | 5 | 2 | 2 | 3 | 3 |
|   | 6.3 | 5 | 5 | 5 | 5 | 5 | 5 | 5 | 3 | 3 | 4 | 4 |
| Comparative Compound A | 2.5 | 0 | 0 | 0 | 0 | 0 | 0 | 0 | 0 | 0 | 0 | 0 |
| Comparative Compound B | 2.5 | 0 | 0 | 0 | 0 | 0 | 0 | 0 | 0 | 0 | 0 | 0 |

Comparative Compounds A and B: Disclosed in Japanese Unexamined Patent Publication No. 122671/1988

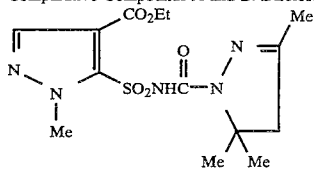

Comparative Compound A

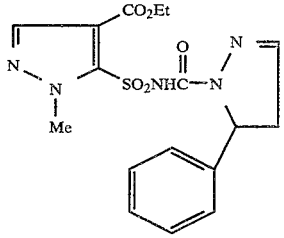

Comparative Compound B

TABLE 3

| Comp. No. | Dose kg/ha | EC | DI | CY | SO | GA | RO | OR | ZE | TR | GL | GO | BE |
|---|---|---|---|---|---|---|---|---|---|---|---|---|---|
| 1 | 0.16 | 4 | 4 | 1 | 5 | 5 | 5 | 4 | 2 | 1 | 4 | 4 | 5 |
|   | 0.32 | 5 | 5 | 2 | 5 | 5 | 5 | 5 | 3 | 1 | 5 | 5 | 5 |
|   | 0.63 | 5 | 5 | 3 | 5 | 5 | 5 | 5 | 4 | 2 | 5 | 5 | 5 |
| 3 | 0.16 | 5 | 4 | 5 | 5 | 5 | 5 | 1 | 0 | 0 | 4 | 4 | 4 |
|   | 0.32 | 5 | 5 | 5 | 5 | 5 | 5 | 2 | 0 | 1 | 5 | 5 | 5 |
|   | 0.63 | 5 | 5 | 5 | 5 | 5 | 5 | 3 | 1 | 2 | 5 | 5 | 5 |
| 4 | 0.63 | 5 | 3 | 2 | 5 | 5 | 5 | 2 | 1 | 1 | 4 | 4 | 5 |
| 5 | 0.16 | 4 | 2 | 1 | 5 | 5 | 5 | 3 | 0 | 0 | 4 | 2 | 4 |
|   | 0.32 | 5 | 3 | 1 | 5 | 5 | 5 | 3 | 1 | 0 | 5 | 3 | 5 |
|   | 0.63 | 5 | 4 | 2 | 5 | 5 | 5 | 4 | 2 | 0 | 5 | 4 | 5 |
| 7 | 0.16 | 1 | 1 | 1 | 5 | 5 | 5 | 4 | 1 | 0 | 1 | 4 | 3 |

TABLE 3-continued

| Comp. No. | Dose kg/ha | EC | DI | CY | SO | GA | RO | OR | ZE | TR | GL | GO | BE |
|---|---|---|---|---|---|---|---|---|---|---|---|---|---|
| | 0.32 | 2 | 2 | 2 | 5 | 5 | 5 | 5 | 2 | 1 | 2 | 5 | 4 |
| | 0.63 | 3 | 3 | 3 | 5 | 5 | 5 | 5 | 2 | 1 | 3 | 5 | 5 |
| 8 | 0.16 | 4 | 1 | 1 | 5 | 5 | 5 | 3 | 1 | 0 | 4 | 2 | 3 |
| | 0.32 | 5 | 2 | 2 | 5 | 5 | 5 | 4 | 1 | 0 | 5 | 3 | 4 |
| | 0.63 | 5 | 4 | 3 | 5 | 5 | 5 | 4 | 3 | 1 | 5 | 4 | 5 |
| 10 | 0.63 | 1 | 2 | 1 | 5 | 5 | 5 | 0 | 0 | 0 | 5 | 3 | 5 |
| 13 | 0.16 | 3 | 2 | 1 | 5 | 5 | 5 | 2 | 0 | 1 | 5 | 2 | 3 |
| | 0.32 | 4 | 3 | 2 | 5 | 5 | 5 | 3 | 1 | 2 | 5 | 3 | 4 |
| | 0.63 | 5 | 4 | 3 | 5 | 5 | 5 | 4 | 2 | 3 | 5 | 4 | 5 |
| 15 | 0.63 | 2 | 1 | 1 | 5 | 5 | 5 | 0 | 1 | 1 | 4 | 3 | 4 |
| 18 | 0.63 | 2 | 1 | 1 | 5 | 5 | 5 | 0 | 1 | 0 | 4 | 2 | 3 |
| 19 | 0.16 | 2 | 1 | 1 | 5 | 5 | 5 | 0 | 0 | 0 | 4 | 4 | 3 |
| | 0.32 | 3 | 2 | 2 | 5 | 5 | 5 | 0 | 1 | 1 | 5 | 5 | 4 |
| | 0.63 | 4 | 4 | 3 | 5 | 5 | 5 | 1 | 2 | 2 | 5 | 5 | 5 |
| 20 | 0.16 | 1 | 0 | 0 | 4 | 5 | 5 | 0 | 0 | 0 | 4 | 2 | 2 |
| | 0.32 | 2 | 1 | 1 | 5 | 5 | 5 | 1 | 0 | 1 | 5 | 3 | 3 |
| | 0.63 | 3 | 2 | 2 | 5 | 5 | 5 | 2 | 1 | 2 | 5 | 4 | 4 |
| 21 | 0.16 | 0 | 0 | 0 | 4 | 5 | 5 | 0 | 0 | 0 | 4 | 3 | 4 |
| | 0.32 | 1 | 1 | 0 | 5 | 5 | 5 | 1 | 0 | 1 | 5 | 4 | 5 |
| | 0.63 | 2 | 2 | 1 | 5 | 5 | 5 | 2 | 0 | 2 | 5 | 5 | 5 |
| 22 | 0.63 | 2 | 1 | 1 | 5 | 5 | 5 | 2 | 1 | 2 | 4 | 3 | 3 |
| 28 | 1.6 | 3 | 3 | 1 | 5 | 5 | 5 | 1 | 0 | 0 | 4 | 4 | 4 |
| | 3.2 | 4 | 4 | 2 | 5 | 5 | 5 | 2 | 1 | 1 | 5 | 5 | 5 |
| | 6.3 | 5 | 5 | 2 | 5 | 5 | 5 | 3 | 2 | 2 | 5 | 5 | 5 |
| Comparative Compound A | 2.5 | 0 | 0 | 0 | 0 | 2 | 0 | 0 | 0 | 0 | 0 | 0 | 0 |
| Comparative Compound B | 2.5 | 0 | 0 | 0 | 0 | 1 | 0 | 0 | 0 | 0 | 0 | 0 | 0 |

Comparative Compounds A and B: Disclosed in Japanese Unexamined Patent Publication No. 122671/1988.

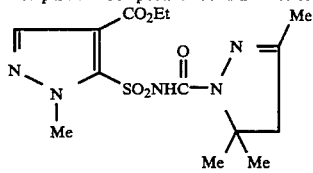

Comparative Compound A

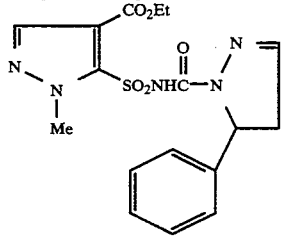

Comparative Compound B

TABLE 4

| No. | g/a | TR | AV | AL |
|---|---|---|---|---|
| 3 | 0.4 | 0 | 4 | 4 |
| | 0.8 | 0 | 5 | 5 |
| | 1.6 | 0 | 5 | 5 |
| 19 | 0.4 | 0 | 3 | 3 |
| | 0.8 | 0 | 4 | 4 |
| | 1.6 | 0 | 5 | 5 |
| 21 | 0.4 | 0 | 3 | 3 |
| | 0.8 | 0 | 4 | 4 |
| | 1.6 | 0 | 5 | 5 |
| Reference* Compound | 0.4 | 0 | 0 | 0 |
| | 0.8 | 0 | 1 | 1 |
| | 1.6 | 0 | 2 | 2 |

*Diclofop-methyl

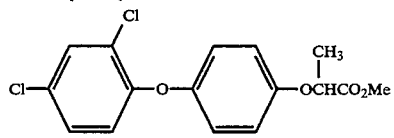

We claim:

1. A pyridinesulfonamide derivative of the formula (I) or a salt thereof:

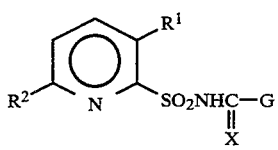

(I)

wherein $R^1$ is a halogen atom, a trifluoromethyl group, a $C_1-C_6$ alkoxycarbonyl group, a $C_1-C_6$ mono- or di-alkylaminocarbonyl group, a $C_1-C_6$ alkoxy group, a $C_1-C_6$ alkylsulfonyl group, a $C_1-C_6$ alkylthio group, a $C_1-C_6$ alkyl group substituted by a $C_1-C_6$ alkoxy group, a $C_1-C_6$ alkyl group substituted by a $C_1-C_6$ mono- or poly-halogenoalkoxy group, a $C_1-C_6$ mono- or poly-halogenoalkoxy group, a $C_1-C_6$ mono- or di-alkylaminosulfonyl group, a $C_1-C_6$ alkoxyaminosulfonyl group substituted by a $C_1-C_6$ alkyl group, a nitro group, a $C_1-C_6$ alkyl group substituted by a $C_1-C_6$ alkylthio group, a $C_1-C_6$ alkyl group substituted by a $C_1-C_6$ alkylsulfonyl group, or a $C_1$-$C_6$ alkyl group substituted by a $C_1$-$C_6$ alkoxycarbonyl group;
$R^2$ is a hydrogen atom or a halogen atom;
X is an oxygen atom or a sulfur atom; and
G is

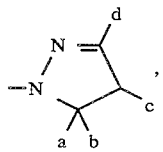

wherein one of a, b, c and d represents a furan, thiophene or naphthyl group and the other remaining a, b, c or d each represent a hydrogen atom, a $C_1$-$C_6$ alkyl group, a $C_2$-$C_6$ alkenyl group, a $C_2$-$C_6$ alkynyl group, a $C_1$-$C_6$ alkyl group mono- or poly-substituted by a halogen atom, a $C_1$-$C_6$ alkoxy group, a $C_1$-$C_6$ alkyl group substituted by a $C_1$-$C_6$ alkoxy group, a $C_1$-$C_6$ alkoxycarbonyl group, a $C_1$-$C_6$ alkyl group substituted by a $C_1$-$C_6$ alkylthio group, a $C_1$-$C_6$ alkyl group substituted by a $C_1$-$C_6$ alkylsulfonyl group, a $C_1$-$C_6$ alkylthio group, a $C_1$-$C_6$ alkylcarbonyl group, a $C_3$-$C_7$ cycloalkyl group, a $C_3$-$C_7$ cycloalkenyl group or a cyano group, and which furan or thiophene may be mono- or poly-substituted by a $C_1$-$C_6$ alkyl group, a $C_1$-$C_6$ alkoxy group, a halogen atom, a trifluoromethyl group, a nitro group or a $C_1$-$C_6$ alkoxycarbonyl group.

2. A herbicide containing an effective amount of the compound of claim 1, as an active ingredient in admixture with a carrier.

3. A method of treating crop plants which comprises administering a herbicidally effective amount of the compound of claim 1 as an active ingredient.

4. A compound of formula II

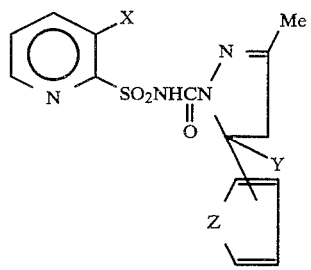

wherein X is a trifluoromethyl group or a halogen atom; Y is a hydrogen atom or a methyl group; Z is a sulfur atom or an oxygen atom.

5. A herbicide containing an effective amount of the compound of claim 4 as an active ingredient in admixture with a carrier.

6. A method of treating crop plants which comprises administering a herbicidally effective amount of the compound of claim 4 as an active ingredient.

7. The pyridinesulfonamide derivative of claim 4, which is

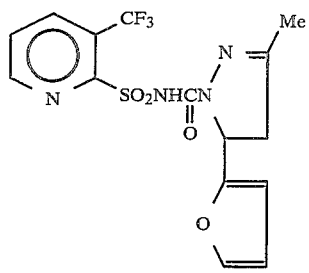

8. The pyridinesulfonamide derivative of claim 4, which is

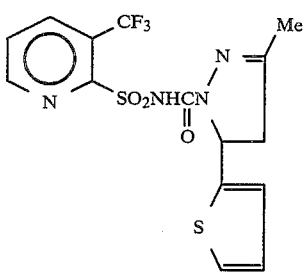

9. The pyridinesulfonamide derivative of claim 4, which is

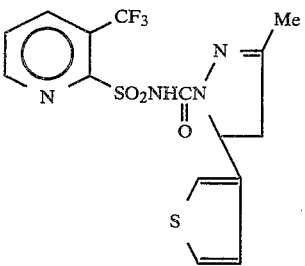

10. The pyridinesulfonamide derivative of claim 4, which is

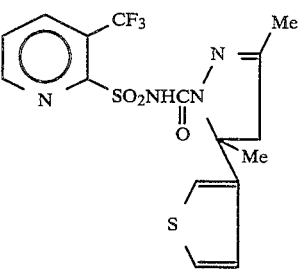

11. The pyridinesulfonamide derivative of claim 4, which is

12. The pyridinesulfonamide derivative of claim 4, which is
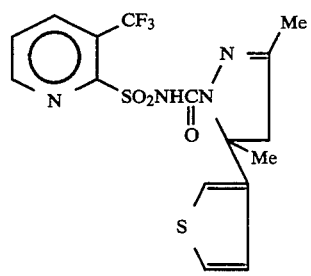
13. The pyridinesulfonamide derivative of claim 4, which is
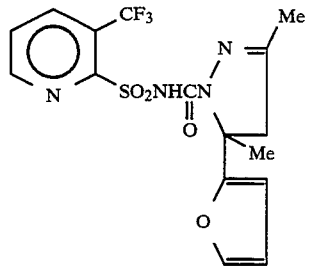
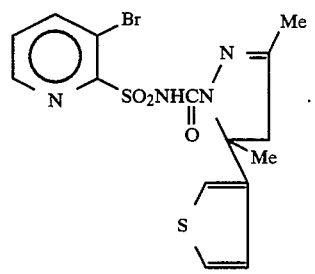
* * * * *